United States Patent
Lee et al.

(10) Patent No.: US 10,973,424 B2
(45) Date of Patent: Apr. 13, 2021

(54) CHARGING METHOD USING EXTERNAL ELECTRODE SWITCHING BETWEEN BIOMETRIC SENSOR AND CHARGING CIRCUIT, AND ELECTRONIC DEVICE USING THE SAME

(71) Applicant: Samsung Electronics Co., Ltd., Suwon-si (KR)

(72) Inventors: June Lee, Suwon-si (KR); Ju-Hyup Lee, Hwaseong-si (KR); Jae-Won Choi, Incheon (KR); Tae-Hyun Woo, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 202 days.

(21) Appl. No.: 15/975,185

(22) Filed: May 9, 2018

(65) Prior Publication Data

US 2018/0360326 A1    Dec. 20, 2018

(30) Foreign Application Priority Data

Jun. 14, 2017    (KR) .......................... 10-2017-0074941

(51) Int. Cl.
*H02J 7/00* (2006.01)
*A61B 5/02* (2006.01)
(Continued)

(52) U.S. Cl.
CPC ............... *A61B 5/0245* (2013.01); *A61B 5/02* (2013.01); *A61B 5/681* (2013.01); *G06F 3/01* (2013.01);
(Continued)

(58) Field of Classification Search
CPC ... A61B 5/0245; A61B 5/681; A61B 5/02444; A61B 5/02; G06F 3/0346; G06F 3/011;
(Continued)

(56) References Cited

U.S. PATENT DOCUMENTS 4,513,753 A * 4/1985 Tabata ................. A61B 5/0404
600/519
5,072,167 A * 12/1991 Zias ...................... H02J 7/0034
320/165
(Continued)

FOREIGN PATENT DOCUMENTS

KR        10-0491650 B1    5/2005

*Primary Examiner* — John T Trischler
(74) *Attorney, Agent, or Firm* — Jefferson IP Law, LLP

(57) ABSTRACT

A charging method using an electrode of a biometric sensor, and an electronic device using the same. A wearable electronic device includes a housing, at least one electrode exposed outwards from one surface of the housing, a battery provided inside the housing, a charger circuit connected electrically to the battery, at least one sensor, a switch configured to connect the charger circuit or the at least one sensor to the at least one electrode, and a processor connected electrically to the charger circuit, the at least one sensor, and the switch. The processor is configured to determine whether the wearable electronic device is coupled to a body, based on a signal acquired through the at least one sensor, and control the switch to connect the charger circuit or the at least one sensor to the at least one electrode in correspondence with a result of the determination.

11 Claims, 17 Drawing Sheets

(51) Int. Cl.
*A61B 5/0245* (2006.01)
*H04N 5/225* (2006.01)
*H01M 10/44* (2006.01)
*G06F 3/01* (2006.01)
*H01M 10/04* (2006.01)
*H02J 7/02* (2016.01)
*A61B 5/00* (2006.01)
*G06F 3/0346* (2013.01)
*H02J 50/00* (2016.01)
*A61B 5/024* (2006.01)
*H02J 50/10* (2016.01)
*H02J 50/80* (2016.01)
*H02J 50/12* (2016.01)
*A61B 5/026* (2006.01)

(52) U.S. Cl.
CPC ............ *G06F 3/011* (2013.01); *G06F 3/0346* (2013.01); *H01M 10/0431* (2013.01); *H01M 10/44* (2013.01); *H02J 7/0042* (2013.01); *H02J 7/0068* (2013.01); *H02J 7/025* (2013.01); *H02J 50/00* (2016.02); *H04N 5/2258* (2013.01); *A61B 5/024* (2013.01); *A61B 5/026* (2013.01); *A61B 5/0261* (2013.01); *A61B 5/02416* (2013.01); *A61B 5/02444* (2013.01); *A61B 2560/0204* (2013.01); *H02J 50/10* (2016.02); *H02J 50/12* (2016.02); *H02J 50/80* (2016.02)

(58) Field of Classification Search
CPC . G06F 3/01; H02J 7/0042; H02J 7/025; H02J 50/00; H04N 5/2258; H01M 10/44; H01M 10/0431
USPC .......................................................... 320/114
See application file for complete search history.

(56) References Cited

U.S. PATENT DOCUMENTS

| | | | | |
|---|---|---|---|---|
| 8,155,368 B2* | 4/2012 | Cheung | ................ | H04R 5/0335 379/430 |
| 8,363,425 B2* | 1/2013 | Rupert | ................ | H01M 10/486 180/2.1 |
| 8,954,099 B2* | 2/2015 | Forutanpour | ......... | G06F 1/1626 455/466 |
| 9,197,082 B1* | 11/2015 | Zhang | ................ | G16H 40/63 |
| 9,211,076 B2* | 12/2015 | Kim | ................ | A61B 5/0416 |
| 9,237,869 B1* | 1/2016 | Lee | ................ | A61B 5/6804 |
| 9,263,903 B2 | 2/2016 | Newton | | |
| 9,276,625 B2* | 3/2016 | Jing | ................ | H04M 1/0202 |
| 9,287,728 B2* | 3/2016 | Odaohhara | ......... | H01M 10/443 |
| 9,442,523 B2* | 9/2016 | Lee | ................ | G06F 1/163 |
| 9,484,736 B2* | 11/2016 | Hong | ................ | H02H 5/083 |
| 9,590,433 B2* | 3/2017 | Li | ................ | H04M 1/18 |
| 9,591,913 B2* | 3/2017 | Kim | ................ | G04B 37/084 |
| 9,594,404 B2* | 3/2017 | Yoon | ................ | G01R 33/07 |
| 9,629,574 B2* | 4/2017 | Lee | ................ | A61B 5/1118 |
| 9,768,628 B2* | 9/2017 | Fish | ................ | H02J 7/0042 |
| 9,861,280 B2* | 1/2018 | Lee | ................ | A61B 5/681 |
| 9,872,525 B2* | 1/2018 | Lee | ................ | A41D 1/002 |
| 9,872,619 B2* | 1/2018 | Lee | ................ | A61B 5/0006 |
| 9,874,457 B2* | 1/2018 | Fung | ................ | A61B 5/1118 |
| 9,883,730 B2* | 2/2018 | Lee | ................ | A45F 5/00 |
| 9,891,667 B2* | 2/2018 | Jung | ................ | G06F 1/1633 |
| 9,899,832 B2* | 2/2018 | Kuo | ................ | G06F 1/163 |
| 9,962,082 B2* | 5/2018 | Kim | ................ | A61B 5/6803 |
| 10,008,870 B2* | 6/2018 | Davison | ................ | H04B 1/3883 |
| 10,103,541 B2* | 10/2018 | Kuo | ................ | G06F 1/163 |
| 10,128,670 B2* | 11/2018 | Ban | ................ | H02J 7/0031 |
| 10,477,354 B2* | 11/2019 | Patel | ................ | A61B 5/6801 |
| 10,585,467 B2* | 3/2020 | Moon | ................ | G01R 31/3835 |
| 2005/0196003 A1* | 9/2005 | Fluit | ................ | H02J 7/0034 381/323 |
| 2006/0229520 A1* | 10/2006 | Yamashita | ........... | A61B 5/0002 600/503 |
| 2007/0191719 A1* | 8/2007 | Yamashita | ........... | A61B 5/0002 600/503 |
| 2009/0085514 A1* | 4/2009 | Mizoguchi | ............ | H02J 7/0042 320/113 |
| 2009/0274335 A1* | 11/2009 | Cheung | ................ | H04R 5/0335 381/374 |
| 2010/0089846 A1* | 4/2010 | Navarro Ruiz | ......... | B60L 53/36 211/4 |
| 2011/0050175 A1* | 3/2011 | Odaohhara | ......... | H01M 10/443 320/134 |
| 2011/0090666 A1* | 4/2011 | Rupert | ................ | H01M 10/486 361/829 |
| 2011/0215931 A1* | 9/2011 | Callsen | ................ | F41H 1/04 340/573.1 |
| 2011/0218756 A1* | 9/2011 | Callsen | ................ | F41H 1/04 702/139 |
| 2011/0312349 A1* | 12/2011 | Forutanpour | ......... | G06F 1/1626 455/466 |
| 2011/0316353 A1* | 12/2011 | Ichikawa | ................ | H02J 7/0044 307/149 |
| 2012/0078071 A1* | 3/2012 | Bohm | ................ | G06F 1/3203 600/345 |
| 2013/0015824 A1* | 1/2013 | Newton | ................ | H02J 7/0034 320/165 |
| 2013/0020986 A1* | 1/2013 | Linzon | ................ | H02J 5/00 320/107 |
| 2013/0118255 A1* | 5/2013 | Callsen | ................ | A42B 3/046 73/491 |
| 2013/0211290 A1* | 8/2013 | Lee | ................ | A43B 3/0005 600/592 |
| 2013/0310677 A1* | 11/2013 | Chiu | ................ | A61B 5/021 600/384 |
| 2014/0239904 A1* | 8/2014 | Tanaka | ................ | B60R 16/04 320/128 |
| 2014/0247155 A1* | 9/2014 | Proud | ................ | A61B 5/1118 340/870.16 |
| 2014/0307356 A1* | 10/2014 | Hong | ................ | H02H 5/083 361/78 |
| 2014/0371611 A1* | 12/2014 | Kim | ................ | A61B 5/0416 600/509 |
| 2015/0137731 A1* | 5/2015 | Kim | ................ | H02J 7/35 320/101 |
| 2015/0181324 A1* | 6/2015 | Hsieh | ................ | H04R 1/105 381/74 |
| 2015/0188347 A1* | 7/2015 | Ruan | ................ | H02J 7/0063 320/118 |
| 2015/0189976 A1* | 7/2015 | Lee | ................ | A45F 5/00 224/267 |
| 2015/0270734 A1* | 9/2015 | Davison | ................ | H02J 7/0044 320/103 |
| 2015/0340891 A1* | 11/2015 | Fish | ................ | H02J 7/342 320/103 |
| 2015/0345985 A1* | 12/2015 | Fung | ................ | G06F 19/00 702/160 |
| 2016/0026212 A1* | 1/2016 | Lee | ................ | G06F 1/163 361/679.03 |
| 2016/0058375 A1 | 3/2016 | Rothkopf | | |
| 2016/0099613 A1* | 4/2016 | Bell | ................ | H02J 7/025 307/104 |
| 2016/0112775 A1* | 4/2016 | Kim | ................ | A61B 5/0002 340/870.07 |
| 2016/0120463 A1* | 5/2016 | Chen | ................ | A61B 5/02438 600/479 |
| 2016/0128209 A1 | 5/2016 | Yoon et al. | | |
| 2016/0151007 A1* | 6/2016 | Tateda | ................ | A61B 5/00 600/476 |
| 2016/0162721 A1* | 6/2016 | Lee | ................ | G06K 9/0002 382/124 |
| 2016/0192716 A1* | 7/2016 | Lee | ................ | G06F 3/015 2/422 |
| 2016/0192856 A1* | 7/2016 | Lee | ................ | A61B 5/6804 600/384 |

(56) References Cited

U.S. PATENT DOCUMENTS

| | | | |
|---|---|---|---|
| 2016/0192857 A1* | 7/2016 | Lee | A61B 5/681 |
| | | | 600/382 |
| 2016/0206212 A1* | 7/2016 | Lee | A61B 5/0205 |
| 2016/0241059 A1* | 8/2016 | Li | H04M 1/18 |
| 2016/0249174 A1 | 8/2016 | Patel et al. | |
| 2016/0255733 A1* | 9/2016 | Jung | G06F 1/1633 |
| | | | 361/759 |
| 2016/0284961 A1* | 9/2016 | Alhawari | H01L 35/28 |
| 2016/0308583 A1* | 10/2016 | Hsu | H04B 5/0025 |
| 2016/0317067 A1* | 11/2016 | Lee | A61B 5/1118 |
| 2016/0367138 A1 | 12/2016 | Kim et al. | |
| 2016/0378069 A1* | 12/2016 | Rothkopf | G06F 1/1643 |
| | | | 368/10 |
| 2016/0378070 A1* | 12/2016 | Rothkopf | G06F 1/1643 |
| | | | 368/10 |
| 2016/0378071 A1* | 12/2016 | Rothkopf | G06F 1/1643 |
| | | | 368/10 |
| 2017/0054289 A1* | 2/2017 | Kuo | G06F 1/163 |
| 2017/0054290 A1* | 2/2017 | Di | H02J 7/00 |
| 2017/0054308 A1* | 2/2017 | Olah | H02J 7/32 |
| 2017/0063107 A1* | 3/2017 | Lee | G16H 40/67 |
| 2017/0063117 A1* | 3/2017 | Ban | G01R 27/22 |
| 2017/0085296 A1* | 3/2017 | Hsu | H04B 5/0031 |
| 2017/0172448 A1* | 6/2017 | Shin | A61B 5/0022 |
| 2017/0296088 A1* | 10/2017 | Choi | A61B 5/02055 |
| 2018/0028090 A1* | 2/2018 | Tremblay | A61B 5/04001 |
| 2018/0120892 A1* | 5/2018 | von Badinski | G06F 3/1423 |
| 2018/0212449 A1* | 7/2018 | Park | A61B 5/0245 |
| 2019/0073009 A1* | 3/2019 | Moon | H01M 10/48 |

* cited by examiner

CHARGING METHOD USING EXTERNAL ELECTRODE SWITCHING BETWEEN BIOMETRIC SENSOR AND CHARGING CIRCUIT, AND ELECTRONIC DEVICE USING THE SAME

CROSS-REFERENCE TO RELATED APPLICATION(S)

This application is based on and claims priority under 35 U.S.C. § 119 of a Korean patent application number 10-2017-0074941, filed on Jun. 14, 2017, in the Korean Intellectual Property Office, the entire disclosure of which is incorporated by reference herein in its entirety.

TECHNICAL FIELD

The disclosure relates to a charging method using an electrode of a biometric sensor, and an electronic device using the same.

BACKGROUND

More services and more additional functions have been provided through portable electronic devices such as smartphones. To increase the utility of such electronic devices and satisfy various demands of users, communication service providers or electronic device manufacturers have competed to develop electronic devices which provide various functions and which are differentiated from those of other companies.

As the performance of electronic devices has been increasing, various biometric techniques are applied to portable electronic devices. Users may acquire physical information or health information about themselves by the biometric techniques applied to the electronic devices.

A portable electronic device to which various biometric techniques are applied may be operated with a rechargeable battery in view of the nature of the portable electronic device, and may charge the battery with a separate charger.

Biometric techniques may be applied to an electronic device through various types of interfaces. For example, the electronic device may measure at least one of a pulse or heart rate of a user based on information acquired through an optical sensor. The electronic device may also measure at least one of the body fat percentage, electrocardiogram (ECG), or skin resistance of the user based on a signal acquired through an electrode.

A portable electronic device including at least one of such an optical sensor or electrode may be provided with a contact terminal to receive power from a charger. The portable electronic device and the charger may be electrically connected to each other through contact terminals thereof, and the portable electronic device may charge a battery with power received from the charger.

The electrode used to acquire physical information or health information about the user and the contact terminal used to charge the battery execute different functions. Accordingly, the portable electronic device should be provided with the electrode and the contact terminal separately. In this case, the miniaturization of the portable electronic device may be limited. When the electrode and the contact terminal are mounted on the same plane of the portable electronic device, there may be limitations in designing the portable electronic device.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide a portable electronic device including at least one electrode available for acquiring physical information or health information about a user, and for charging a battery as well.

Another aspect of the disclosure is to provide a charger (e.g., a cradle) for supplying power to a portable electronic device through at least one electrode used to acquire physical information or health information about a user.

In accordance with an aspect of the disclosure, a wearable electronic device is provided. The wearable electronic device includes a housing, at least one electrode exposed outwards from one surface of the housing, a battery provided inside the housing, a charger circuit connected electrically to the battery, at least one sensor, a switch configured to connect the charger circuit or the at least one sensor to the at least one electrode, and a processor connected electrically to the charger circuit, the at least one sensor, and the switch. The processor is configured to determine whether the wearable electronic device is coupled to a body, based on a signal acquired through the at least one sensor, and control the switch to connect the charger circuit or the at least one sensor to the at least one electrode in correspondence with a result of the determination.

In accordance with another aspect of the disclosure, an electronic device configured to allow an external device to be detachably cradled thereon is provided. The electronic device includes a housing, a power interface provided inside the housing, and configured to change power received from an external power source to power of a predetermined level and output the power of the predetermined level, a plurality of first conductive members connected electrically to the power interface, and configured to transfer power externally, a plurality of second conductive members configured to determine whether the electronic device and the external device are coupled to each other, and a control circuit connected electrically to the power interface, the plurality of first conductive members, and the plurality of second conductive members.

In accordance with another aspect of the disclosure, a wearable electronic device is provided. The wearable electronic device includes a housing including a first surface facing in a first direction, a second surface facing in a second direction opposite to the first direction, and a side surface surrounding at least a part of a space between the first surface and the second surface, a first conductive member exposed outwards from the first surface of the housing, a second conductive member exposed outwards from the second surface of the housing, a charger circuit provided inside the housing, and connected electrically to at least one of the first conductive member or the second conductive member, a first sensor provided inside the housing, and connected electrically to at least one of the first conductive member or the second conductive member, a control circuit connected electrically to the first conductive member, the second conductive member, and the charger circuit, and a coupling member connected to a part of the housing, and configured to detachably couple the wearable electronic device to a part of a user's body.

In accordance with another aspect of the disclosure, a method for controlling a wearable electronic device including at least one electrode is provided. The method includes determining whether the wearable electronic device is coupled to a body, based on a signal acquired through at least one sensor of the wearable electronic device, and controlling a switch of the wearable electronic device to connect a charger circuit of the wearable electronic device or the at least one sensor to the at least one electrode in correspondence with a result of the determination.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, like reference numerals will be understood to refer to like parts, components, and structures.

DETAILED DESCRIPTION

Figure 1:
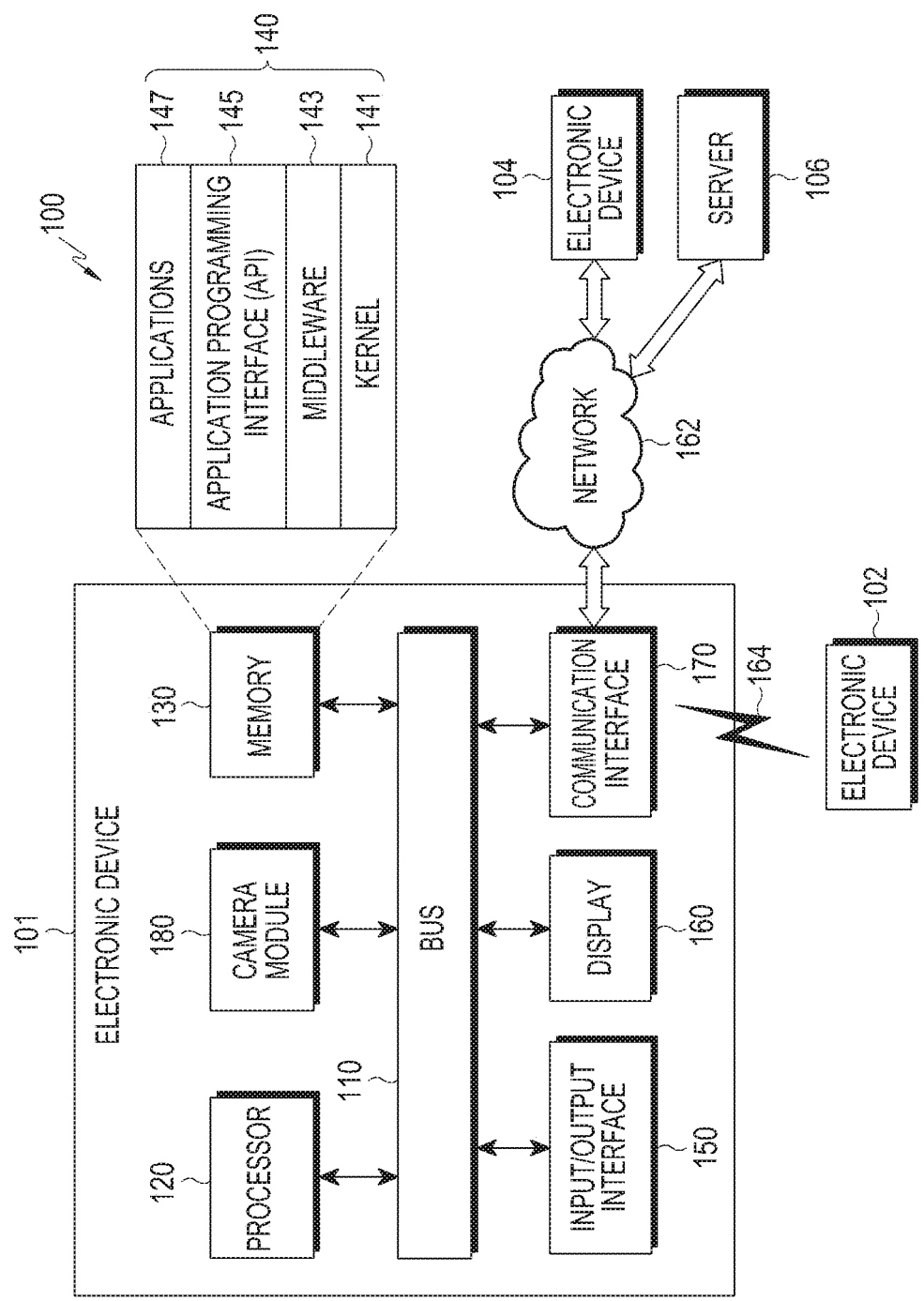
FIG. 1 is a block diagram illustrating an electronic device and a network environment according to an embodiment of the disclosure.

The following description with reference to the accompanying drawings is provided to assist in a comprehensive understanding of various embodiments of the disclosure as defined by the claims and their equivalents. In includes various specific details to assist in that understanding, but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness. In relation to a description of the drawings, like reference numerals denote the same components.

The terms and words used in the following description and claims are not limited to the bibliographical meanings, but are merely used by the inventor to enable a clear and consistent understanding of the disclosure. Accordingly, it should be apparent to those skilled in the art that the following description of various embodiments of the disclosure is provided for illustration purposes only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In the disclosure, the term "A or B", or "at least one of A and/or B" may cover all possible combinations of enumerated items. The term as used in the disclosure, "first" or "second" may be used for the names of components irrespective of sequence or importance. These expressions are used just to distinguish one component from another component, not limiting the components. When it is said that a component (e.g., a first component) is "(operatively or communicatively) coupled with/to" or "connected to" another component (e.g., a second component), it should be understood that the one component is connected to the other component directly or through any other component (e.g., a third component).

The term "configured to" as used herein may be interchangeably used with, for example, the term "suitable for", "having the capacity to", "designed to", "adapted to", "made to", or "capable of" in hardware or software under circumstances. The term "configured to" may mean that a device is "capable of" with another device or part. For example, "a processor configured to execute A, B, and C" may mean a dedicated processor (e.g., an embedded processor) for performing the corresponding operations or a generic-purpose processor (e.g., a central processing unit (CPU) or an application processor (AP)) for performing the operations by executing one or more software programs stored in a memory.

According to various embodiments of the disclosure, an electronic device may be at least one of, for example, a smart phone, a tablet personal computer (PC), a mobile phone, a video phone, an e-book reader, a desktop PC, a laptop PC, a netbook computer, a workstation, a server, a personal digital assistant (PDA), a portable multimedia player (PMP), an MP3 player, medical equipment, a camera, or a wearable device. The wearable device may be at least one of an accessory type (e.g., a watch, a ring, a bracelet, an ankle bracelet, a necklace, glasses, contact lenses, or a head-mounted device (HMD)), a fabric or clothes type (e.g., electronic clothes), an attached type (e.g., a skin pad or a tattoo), or an implantable circuit.

According to various embodiments of the disclosure, an electronic device may be at least one of a television (TV), a digital versatile disc (DVD) player, an audio player, a refrigerator, an air conditioner, a vacuum cleaner, an oven, a microwave oven, a washer, an air purifier, a set-top box, a home automation control panel, a security control panel, a media box (e.g., Samsung HomeSync™, Apple TV™, or Google TV™), a game console (e.g., Xbox™ or PlayStation™), an electronic dictionary, an electronic key, a camcorder, or an electronic picture frame.

According to other embodiments of the disclosure, an electronic device may be at least one of a medical device (e.g., a portable medical meter such as a blood glucose meter, a heart rate meter, a blood pressure meter, or a body temperature meter, a magnetic resonance angiography (MRA) device, a magnetic resonance imaging (MRI) device, a computed tomography (CT) device, an imaging device, or an ultrasonic device), a navigation device, a global navigation satellite system (GNSS), an event data recorder (EDR), a flight data recorder (FDR), an automotive infotainment device, a naval electronic device (e.g., a naval navigation device or a gyrocompass), an avionic electronic device, a security device, an in-vehicle head unit, an industrial or consumer robot, a drone, an automatic teller machine (ATM) in a financial facility, a point of sales (POS) device in a shop, or an Internet of things (IoT) device (e.g., a lighting bulb, various sensors, a sprinkler, a fire alarm, a thermostat, a street lamp, a toaster, sports goods, a hot water tank, a heater, or a boiler).

According to some embodiments of the disclosure, an electronic device may be at least one of furniture, a part of a building/structure or a vehicle, an electronic board, an electronic signature receiving device, a projector, or various measuring devices (e.g., water, electricity, gas or electromagnetic wave measuring devices).

According to various embodiments of the disclosure, an electronic device may be flexible or a combination of two or more of the foregoing devices. According to an embodiment of the disclosure, an electronic device is not limited to the foregoing devices. In the disclosure, the term user may refer to a person or device (e.g., artificial intelligence electronic device) that uses an electronic device.

FIG. 1 is a block diagram illustrating an electronic device and a network environment according to an embodiment of the disclosure.

Referring to FIG. 1, an electronic device 101 in a network environment 100 according to various embodiments is described. The electronic device 101 may include a bus 110, a processor 120, a memory 130, an input/output (I/O) interface 150, a display 160, a communication interface 170, and a camera module 180. In some embodiments, at least one of the components may be omitted in the electronic device 101 or a component may be added to the electronic device 101.

The bus 110 may interconnect the foregoing components 120, 130, 150, 160, and 170, and include a circuit that allows communication (e.g., control messages or data) between the foregoing components.

The processor 120 may include one or more of a CPU, an AP, or a communication processor (CP). The processor 120 may, for example, execute computation or data processing related to control and/or communication of at least one other component of the electronic device 101.

The memory 130 may include a volatile memory and/or a non-volatile memory. The memory 130 may store instructions or data related to at least one other component of the electronic device 101. The memory 130 may store software and/or programs 140.

The programs 140 may include a kernel 141, middleware 143, an application programming interface (API) 145, and/or application programs (or applications) 147. At least a part of the kernel 141, the middleware 143, or the API 145 may be called an operating system (OS). The kernel 141 may control or manage system resources (e.g., the bus 110, the processor 120, or the memory 130) that are used in executing operations or functions implemented in other programs (e.g., the middleware 143, the API 145, or the application programs 147). The kernel 141 may provide an interface for allowing the middleware 143, the API 145, or the application programs 147 to access individual components of the electronic device 101 and control or manage system resources. The middleware 143 may serve as a medium through which the kernel 141 may communicate with, for example, the API 145 or the application programs 147 to transmit and receive data. Further, the middleware 143 may process one or more task requests received from the application programs 147 according to the priority levels of the task requests. For example, the middleware 143 may assign priority levels for using system resources (the bus 110, the processor 120, or the memory 130) of the electronic device 101 to at least one of the application programs 147, and process the one or more task requests according to the priority levels. The API 145 is an interface through which the applications 147 control functions that the kernel 141 or the middleware 143 provides. For example, the API 145 may include at least one interface, function, or command for file control, window control, video processing, or text control.

The I/O interface 150 may provide a command or data received from a user or an external device to the other component(s) of the electronic device 101, or output a command or data received from the other component(s) of the electronic device 101 to the user or the external device.

The display 160 may include a liquid crystal display (LCD), a light emitting diode (LED) display, an organic LED (OLED) display, a microelectromechanical systems (MEMS) display, or an electronic paper display. The display 160 may display various types of content (e.g., text, an image, a video, an icon, and/or a symbol) to the user. The display 160 may include a touch screen and receive, for example, a touch input, a gesture input, a proximity input, or a hovering input through an electronic pen or a user's body part.

The communication interface 170 may establish communication between the electronic device 101 and an external device (e.g., a first external electronic device 102, a second external electronic device 104, or a server 106). For example, the communication interface 170 may be connected to a network 162 by wireless communication or wired communication, and communicate with the external device (e.g., the second external electronic device 104 or the server 106) over the network 162.

The wireless communication may include cellular communication conforming to at least one of long term evolution (LTE), LTE-advanced (LTE-A), code division multiple access (CDMA), wideband CDMA (WCDMA), universal mobile telecommunication system (UMTS), wireless broadband (WiBro), or global system for mobile communications (GSM). The wireless communication may include, for example, at least one of WiFi, LiFi, Bluetooth, Bluetooth low energy (BLE), Zigbee, near field communication (NFC), magnetic secure transmission (MST), radio frequency (RF), or body area network (BAN), as indicated by reference numeral 164 in FIG. 1. The wireless communication may include GNSS. GNSS may be, for example, global positioning system (GPS), global navigation satellite system (Glonass), Beidou navigation satellite system (hereinafter, referred to as "Beidou"), or Galileo, the European global satellite-based navigation system. In the disclosure, the terms "GPS" and "GNSS" are interchangeably used with each other. The wired communication may be conducted in conformance to, for example, at least one of universal serial bus (USB), high definition multimedia interface (HDMI), recommended standard 232 (RS-232), power line communication, or plain old telephone service (POTS). The network 162 may be a telecommunication network, for example, at least one of a computer network (e.g., local area network (LAN) or wide area network (WAN)), the Internet, or a telephone network.

The camera module 180 may include at least one image sensor. The image sensor of the camera module 180 may convert external received light to an electrical signal. The electrical signal may be output to the processor 120 via the bus 110 so as to be processed in the processor 120, or may be stored in the memory 130. The camera module 180 may include a pixel array of a plurality of pixels, and the pixel array may include a photodiode which converts external received light to an analog electrical signal. The image sensor of the camera module 180 may include an analog-to-digital converter (ADC) which converts an analog electrical signal to a digital electrical signal. Further, the image sensor of the camera module 180 may include a circuit for scanning the pixel array of the plurality of pixels. Further, the image sensor of the camera module 180 may include an internal memory. The image sensor may temporarily store a digital electrical signal, that is, data output from a pixel, and output the stored data to an external circuit (e.g., the bus 110, the processor 120, or the memory 130). The image sensor of the camera module 180 may include an interface used for data input/output, and output data to an external circuit according to the output rate of the interface.

Each of the first and second external electronic devices 102 and 104 may be of the same type as or a different type from the electronic device 101. All or a part of operations performed in the electronic device 101 may be performed in one or more other electronic devices (e.g., the electronic devices 102 and 104, or the server 106). If the electronic device 101 is to perform a function or a service automatically or upon request, the electronic device 101 may request at least a part of functions related to the function or the service to another device (e.g., the electronic device 102 or 104, or the server 106), instead of performing the function or the service autonomously, or additionally. The other electronic device (e.g., the electronic device 102 or 104, or the server 106) may execute the requested function or an additional function and provide a result of the function execution to the electronic device 101. The electronic device 101 may provide the requested function or service based on the received result or by additionally processing the received result. For this purpose cloud computing, distributed computing, or client-server computing may be used.

Figure 2:
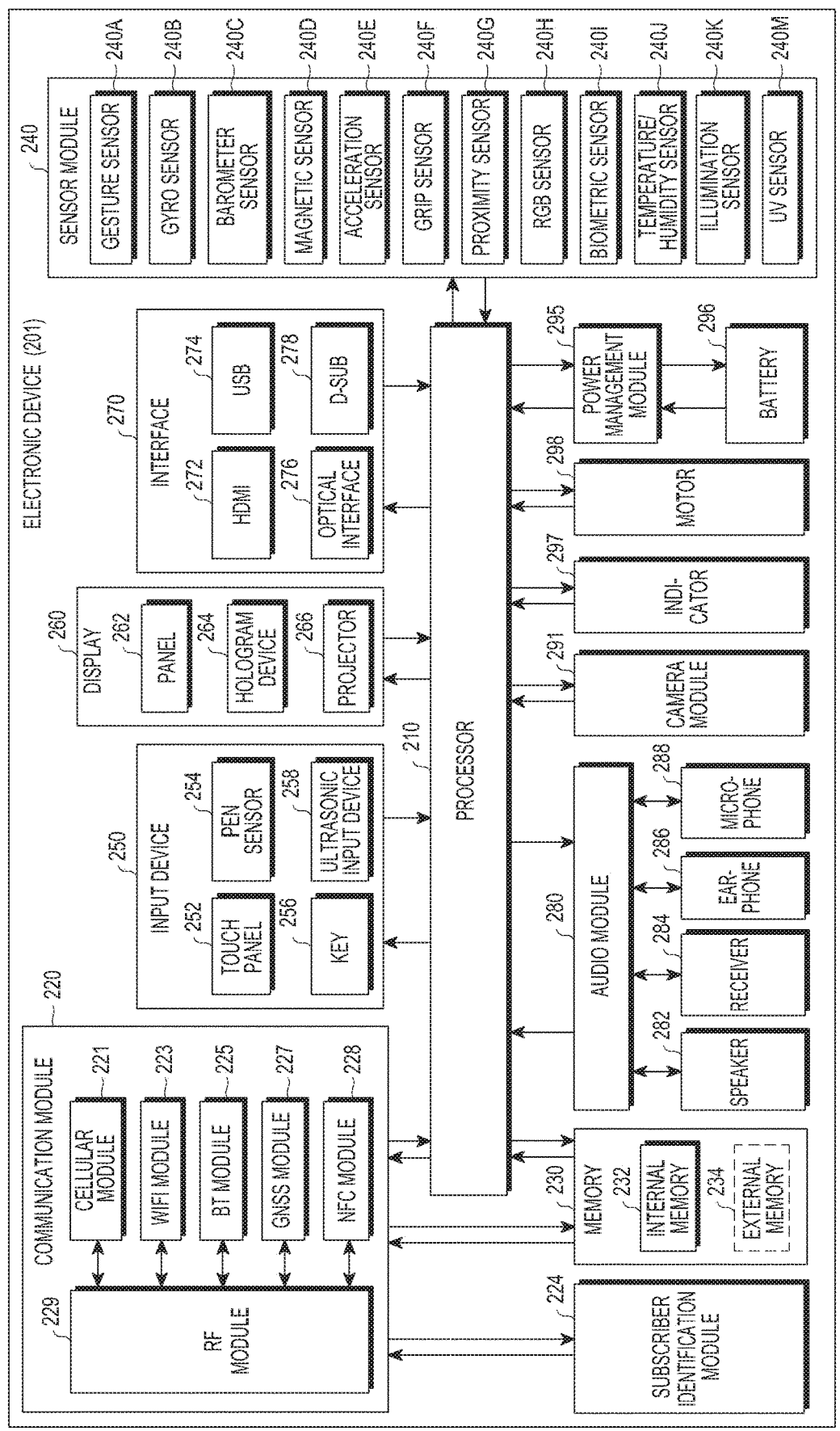
FIG. 2 is a block diagram illustrating an electronic device according to an embodiment of the disclosure.

FIG. 2 is a block diagram of an electronic device according to an embodiment of the disclosure.

Referring to FIG. 2, an electronic device 201 may include the whole or a part of the electronic device 101 illustrated in FIG. 1. The electronic device 201 may include at least one processor (e.g., AP) 210, a communication module 220, a subscriber identification module (SIM) 224, a memory 230, a sensor module 240, an input device 250, a display 260, an interface 270, an audio module 280, a camera module 291, a power management module 295, a battery 296, an indicator 297, and a motor 298.

The processor 210 may control a plurality of hardware or software components that are connected to the processor 210 by executing an OS or an application program, and may perform processing or computation of various types of data. The processor 210 may be implemented as a system on chip (SoC). The processor 210 may further include a graphics processing unit (GPU) and/or an image signal processor. The processor 210 may include at least a part (e.g., a cellular module 221) of the components illustrated in FIG. 2. The processor 210 may load a command or data received from at least one of other components (e.g., a non-volatile memory), process the loaded command or data, and store result data in the non-volatile memory.

The communication module 220 may have the same configuration as or a similar configuration to that of the communication interface 170 illustrated in FIG. 1. The communication module 220 may include the cellular module 221, a WiFi module 223, a Bluetooth (BT) module 225, a GNSS module 227, an NFC module 228, and an RF module 229. The cellular module 221 may provide services such as voice call, video call, text service, or the Internet service, for example, through a communication network. The cellular module 221 may identify and authenticate the electronic device 201 within a communication network, using the SIM (e.g., a SIM card) 224. The cellular module 221 may perform at least a part of the functionalities of the processor 210. The cellular module 221 may include a CP. At least a part (e.g., two or more) of the cellular module 221, the WiFi module 223, the BT module 225, the GNSS module 227, or the NFC module 228 may be included in a single integrated chip (IC) or IC package. The RF module 229 may transmit and receive communication signals (e.g., RF signals). The RF module 229 may include a transceiver, a power amplifier module (PAM), a frequency filter, a low noise amplifier (LNA), an antenna, or the like. At least one of the cellular module 221, the WiFi module 223, the BT module 225, the GNSS module 227, or the NFC module 228 may transmit and receive RF signals via a separate RF module. The SIM 224 may include, for example, a card including the SIM or an embedded SIM. The SIM 224 may include unique identification information (e.g., an integrated circuit card identifier (ICCID)) or subscriber information (e.g., an international mobile subscriber identity (IMSI)).

The memory 230 (e.g., the memory 130) may include an internal memory 232 or an external memory 234. The internal memory 232 may be at least one of a volatile memory (e.g., dynamic RAM (DRAM), static RAM (SRAM), or synchronous dynamic RAM (SDRAM)), and a non-volatile memory (e.g., one time programmable ROM (OTPROM), programmable ROM (PROM), erasable and programmable ROM (EPROM), electrically erasable and programmable ROM (EEPROM), mask ROM, flash ROM, flash memory, a hard drive, or a solid state drive (SSD)). The external memory 234 may include a flash drive such as a compact flash (CF) drive, a secure digital (SD), a micro secure digital (micro-SD), a mini secure digital (mini-SD), an extreme digital (xD), a multi-media card (MMC), or a memory stick. The external memory 234 may be operatively or physically coupled to the electronic device 201 via various interfaces.

The sensor module 240 may measure physical quantities or detect operational states of the electronic device 201, and convert the measured or detected information to electrical signals. The sensor module 240 may include at least one of a gesture sensor 240A, a gyro sensor 240B, a barometer sensor 240C, a magnetic sensor 240D, an accelerometer sensor 240E, a grip sensor 240F, a proximity sensor 240G, a color sensor (e.g., a red, green, blue (RGB) sensor) 240H, a biometric sensor 240I, a temperature/humidity sensor 240J, an illumination sensor 240K, or an ultra violet (UV) sensor 240M. Additionally or alternatively, the sensor module 240 may include, for example, an electrical-nose (E-nose) sensor, an electromyogram (EMG) sensor, an electroencephalogram (EEG) sensor, an electrocardiogram (ECG) sensor, an infrared (IR) sensor, an iris sensor, and/or a finger print sensor. The sensor module 240 may further include a control circuit for controlling one or more sensors included therein. The electronic device 201 may further include a processor configured to control the sensor module 240, as a part of or separately from the processor 210. Thus, while the processor 210 is in a sleep state, the control circuit may control the sensor module 240.

The input device 250 may include a touch panel 252, a (digital) pen sensor 254, a key 256, or an ultrasonic input device 258. The touch panel 252 may operate in at least one of a capacitive, resistive, infrared, or ultrasonic scheme. The touch panel 252 may further include a control circuit. The touch panel 252 may further include a tactile layer to thereby provide haptic feedback to the user. The (digital) pen sensor 254 may include a detection sheet which is a part of the touch panel or separately configured from the touch panel. The key 256 may include a physical button, an optical key, or a keypad. The ultrasonic input device 258 may sense ultrasonic waves generated by an input tool using a microphone (e.g., a microphone 288), and identify data corresponding to the sensed ultrasonic waves.

The display 260 (e.g., the display 160) may include a panel 262, a hologram device 264, a projector 266, and/or a control circuit for controlling the components. The panel 262 may be configured to be, for example, flexible, transparent, or wearable. The panel 262 and the touch panel 252 may be implemented as one or more modules. The panel 262 may include a pressure sensor (or a force sensor) for measuring the strength of the pressure of a user touch. The pressure sensor may be integrated with the touch panel 252, or configured as one or more sensors separately from the touch panel 252. The hologram device 264 may utilize the interference of light waves to provide a three-dimensional image in empty space. The projector 266 may display an image by projecting light on a screen. The screen may be positioned inside or outside the electronic device 201.

The interface 270 may include an HDMI 272, a USB 274, an optical interface 276, or a D-subminiature (D-sub) 278. The interface 270 may be included in the communication interface 170 illustrated in FIG. 1. Additionally or alternatively, the interface 270 may include a mobile high-definition link (MHL) interface, an SD/multimedia card (MMC) interface, or an infrared data association (IrDA) interface.

The audio module 280 may convert a sound to an electrical signal, and vice versa. At least a part of the components of the audio module 280 may be included in the I/O interface 150 illustrated in FIG. 1. The audio module 280 may process sound information input into, or output from a speaker 282, a receiver 284, an earphone 286, or the microphone 288.

The camera module 291 may capture, for example, still images and a video. The camera module 291 may include one or more image sensors (e.g., a front sensor or a rear sensor), a lens, an image signal processor (ISP), or a flash (e.g., an LED or a xenon lamp). According to an embodiment, the camera module 291 may include the whole or a part of the camera module 180.

The power management module 295 may manage power of the electronic device 201. The power management module 295 may include a power management integrated circuit (PMIC), a charger IC, or a battery or fuel gauge. The PMIC may adopt wired and/or wireless charging. The wireless charging may be performed, for example, in a magnetic resonance scheme, a magnetic induction scheme, or an electromagnetic wave scheme, and may further include an additional circuit for wireless charging, for example, a coil loop, a resonant circuit, or a rectifier. The battery gauge may measure, for example, a residual power level, a voltage while charging, current, or temperature of the battery 296. The battery 296 may include, for example, a rechargeable battery and/or a solar battery.

The indicator 297 may indicate specific states of the electronic device 201 or a part of the electronic device 201 (e.g., the processor 210), such as boot status, message status, or charge status. The motor 298 may convert an electrical signal to mechanical vibrations, and generate vibrations, a haptic effect, or the like. The electronic device 201 may include a mobile TV support device (e.g., a GPU) for processing media data compliant with digital multimedia broadcasting (DMB), digital video broadcasting (DVB), or MediaFLO™. Each of the above-described components of the electronic device may include one or more parts, and the name of the component may vary with the type of the electronic device. Some components may be omitted from or added to the electronic device (e.g., the electronic device 201). One entity may be configured by combining a part of the components of the electronic device, to thereby perform the same functions of the components prior to the combining.

A wearable electronic device (e.g., the electronic device 101 illustrated in FIG. 1 or the electronic device 201 illustrated in FIG. 2) according to various embodiments of the disclosure may include a housing, at least one electrode exposed outwards from one surface of the housing, a battery (e.g., the battery 296 illustrated in FIG. 2) provided inside the housing, a charger IC (e.g., the power management module 295 illustrated in FIG. 2) connected electrically to the battery, at least one sensor (e.g., the sensor module 240 illustrated in FIG. 2), a switch connecting the charger IC or the at least one sensor to the at least one electrode, and a processor (e.g., the processor 120 illustrated in FIG. 1 or the processor 210 illustrated in FIG. 2) connected electrically to the charger IC, the at least one sensor, and the switch. The processor 120 may be configured to determine whether the wearable electronic device is coupled to a body based on a signal acquired through the at least one sensor (e.g., the grip sensor 240F illustrated in FIG. 2 or the proximity sensor 240G illustrated in FIG. 2), and to control the switch to connect the charger IC or the at least one sensor to the at least one electrode according to a result of the determination.

In the wearable electronic device 101 according to various embodiments of the disclosure, if the processor 120 determines that the wearable electronic device 101 is coupled to a body, the processor 120 may be configured to control the switch so as to connect the at least one sensor (e.g., the biometric sensor 240I illustrated in FIG. 2) to the at least one electrode, and to generate biometric information related to the body based on a signal acquired through the at least one electrode.

In the wearable electronic device 101 according to various embodiments of the disclosure, if the processor 120 determines that the wearable electronic device is not coupled to the body, the processor 120 may be configured to control the switch to connect the charger IC to the at least one electrode.

In the wearable electronic device 101 according to various embodiments of the disclosure, the housing may include a first surface facing in a first direction, a second surface facing in a second direction opposite to the first direction, and a side surface surrounding at least a part of a space between the first surface and the second surface, and the at least one electrode may include first and second electrodes exposed outwards from the first surface of the housing, and third and fourth electrodes exposed outwards from the second surface of the housing.

In the wearable electronic device 101 according to various embodiments of the disclosure, the at least one sensor may be electrically connected to the at least one electrode, and include a first sensor (e.g., the biometric sensor 240I illustrated in FIG. 2) that receives a signal through the at least one electrode, and a second sensor (e.g., the grip sensor 240F illustrated in FIG. 2 or the proximity sensor 240G illustrated in FIG. 2) that receives an external signal through at least one of the first surface or the second surface of the housing.

In the wearable electronic device 101 according to various embodiments of the disclosure, the first sensor may include at least one of a bioelectrical impedance analysis (BIA) sensor, an electrocardiogram (ECG) sensor, or a galvanic skin response (GSR) sensor, and the second sensor may include at least one of an optical sensor or a grip sensor. The sensor included in the first sensor is not limited to the BIA sensor, the ECG sensor, or the GSR sensor, and may be any sensor, as far as the sensor is capable of acquiring and analyzing a biometric signal of a user. The sensor included in the second sensor is not limited to the optical sensor, and may be any sensor, as far as the sensor is capable of measuring a biometric signal by light. Further, the sensor included in the second sensor is not limited to the grip sensor, and may be any sensor like a temperature sensor or an IR sensor, as far as the sensor is capable of sensing whether the wearable electronic device 101 is coupled to a body. In another embodiment, a sensor that may be included in the first sensor or the second sensor, for example, the BIA sensor, the ECG sensor, the GSR sensor, the optical sensor, or the grip sensor may include at least one of an analog front end (AFE), an amplifier (AMP), or various filters.

In the wearable electronic device 101 according to various embodiments of the disclosure, the first and second electrodes exposed outwards from the first surface of the housing, or the third and fourth electrodes exposed outwards from the second surface of the housing may include "L"-shaped or "U"-shaped electrodes which are symmetrical to each other, surrounding the second sensor exposed outwards. The shapes of the electrodes in the wearable electronic device 101 according to various embodiments of the disclosure are not limited to "L" or "U". Rather, a plurality of symmetrical electrodes or electrodes which are capable of charging and measuring a biometric signal although the electrodes are asymmetrical are available as the electrodes.

The wearable electronic device 101 according to various embodiments of the disclosure may further include a groove formed in at least a part of the housing, towards the inside of the wearable electronic device 101, and a terminal disposed inside the groove, and the processor may be configured to control the switch to connect the charger IC to the at least one electrode, based on at least one signal received from an external device through the terminal.

In the wearable electronic device 101 according to various embodiments of the disclosure, upon receipt of a first signal from the external device (e.g., the electronic device 102 or 104 illustrated in FIG. 1) through the terminal, the processor 120 may be configured to control the switch to connect the charger IC to the at least one electrode in a first mode. Upon receipt of a second signal from the external device through the terminal, the processor 120 may be configured to control the switch to connect the charger IC to the at least one electrode in a second mode.

Figure 3:
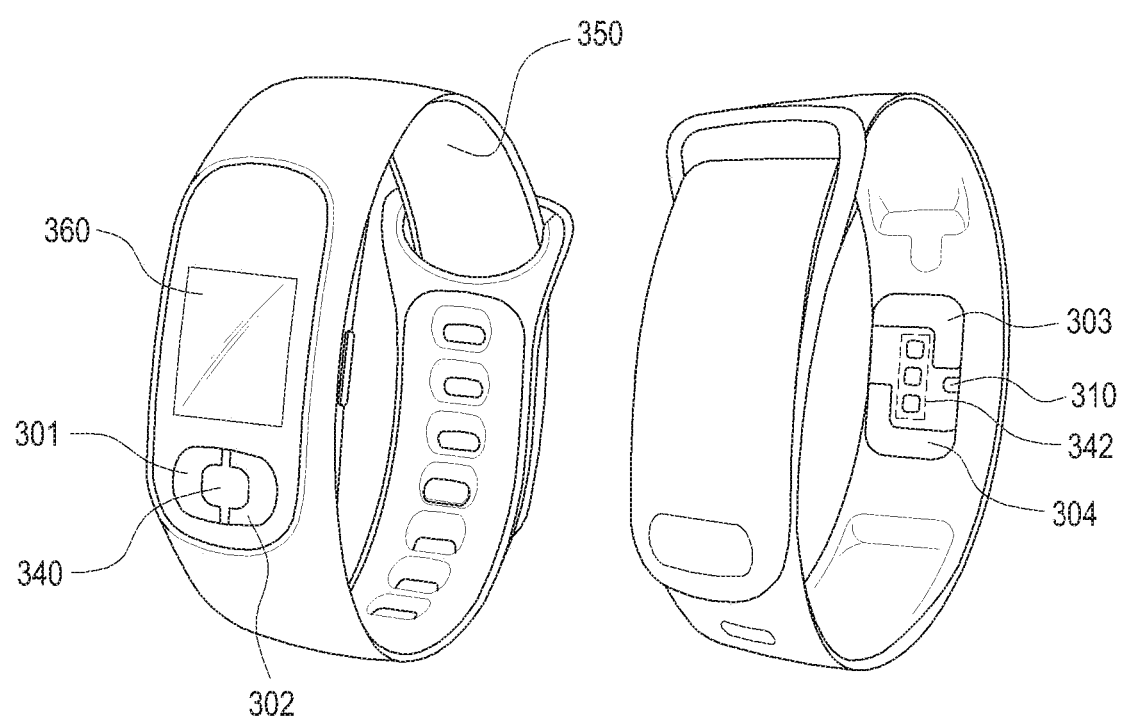
FIG. 3 is a view illustrating the structure of an electronic device according to an embodiment of the disclosure.

FIG. 3 is a view illustrating the structure of an electronic device according to an embodiment of the disclosure. An electronic device according to an embodiment of the disclosure may include at least a part of the components of the electronic device 101 illustrated in FIG. 1 and the components of the electronic device 201 illustrated in FIG. 2.

Referring to FIG. 3, the electronic device 101 according to an embodiment of the disclosure may be a wearable electronic device which may be coupled to a part of a user's body. The electronic device 101 may include at least a part of electrodes 301, 302, 303, and 304, sensor modules 340 and 342, or a display 360. The electronic device 101 may include a housing which includes a first surface facing in a first direction, a second surface facing in a second direction, and a side surface surrounding at least a part of a space between the first surface and the second surface. For example, the first surface of the housing may be a surface including at least one of the first electrode 301 or the second electrode 302, and the second surface of the housing may be a surface including at least one of the third electrode 303 or the fourth electrode 304.

According to an embodiment of the disclosure, the electrodes 301, 302, 303, and 304 may be exposed outwards from at least a part of the housing of the electronic device 101. For example, at least one of the first electrode 301 or the second electrode 302 may be exposed outwards from at least a part of the first surface of the housing of the electronic device 101. Further, at least one of the third electrode 303 or the fourth electrode 304 may be exposed outwards from at least a part of the second surface of the housing of the electronic device 101. The electrodes 301, 302, 303, and 304 may be conductive members in which current may flow. The electrodes 301, 302, 303, and 304 may be configured in various shapes or sizes. The electronic device 101 may include at least one of the electrodes 301, 302, 303, and 304. For example, the electronic device 101 may be configured to include only the two electrodes 303 and 304 on the second surface of the housing. Further, at least one electrode of the electronic device 101 may be disposed on the first surface, the second surface, or any other part of the housing except the first and second surfaces.

According to an embodiment of the disclosure, at least one of the electrodes 301, 302, 303, and 304 may be electrically connected to at least one biometric sensor (e.g., the biometric sensor 240I illustrated in FIG. 2) in the electronic device 101, for use in acquiring physical information or health information about a user. For example, at least one of the electrodes 301, 302, 303, and 304 may be electrically connected to a BIA sensor of the electronic device 101, for use in measuring the body fat rate of the user. Further, at least one of the electrodes 301, 302, 303, and 304 may be electrically connected to an ECG sensor of the electronic device 101, for use in measuring the ECG of the user. At least one of the electrodes 301, 302, 303, and 304 may be electrically connected to a GSR sensor of the electronic device 101, for use in measuring the skin resistance of the user. The above-described sensors which may be connected to at least one of the electrodes 301, 302, 303, and 304 are merely exemplary, and thus should not be construed as limiting the disclosure.

According to an embodiment of the disclosure, at least one of the electrodes 301, 302, 303, and 304 may be electrically connected to a charger IC of the electronic device 101. The charger IC may be a circuit including a power management module (e.g., the power management module 295 illustrated in FIG. 2) or a battery (e.g., the battery 296 illustrated in FIG. 2). Alternatively or additionally, the charger IC may be a circuit that electrically connects at least one component of the electronic device 101 to the power management module (e.g., the power management module 295 illustrated in FIG. 2) or the battery (e.g., the battery 296 illustrated in FIG. 2).

According to an embodiment of the disclosure, the charger IC may be used to charge the battery of the electronic device 101. For example, the charger IC of the electronic device 101 may be connected physically or electrically to an external device (e.g., a charger or a cradle) through at least one of the electrodes 301, 302, 303 and 304 exposed outwards. The charger IC of the electronic device 101 may receive power through at least one of the electrodes 301, 302, 303 and 304, which is connected to an external device.

For example, a part of the outer surface of the third electrode 303 may be connected to a 5-V terminal of an external device that supplies power, and a part of the outer surface of the fourth electrode 304 may be connected to a grounding terminal of the external device that supplies power. In this case, the electronic device may electrically connect the inner surfaces of the third and fourth electrodes 303 and 304 to the charger IC used to charge the battery of the electronic device 101 by controlling a switch included in a circuit of the electronic device 101. In this manner, the electronic device 101 may charge the battery with power received from the external device. According to another embodiment, a part of the outer surface of one of the first and second electrodes 301 and 302 may be connected to the 5-V terminal of the external device that supplies power, and a part of the outer surface of one of the third and fourth electrodes 303 and 304 may be connected to the grounding terminal of the external device that supplies power. In this case, the electronic device may electrically connect the inner surface of the one of the first and second electrodes 301 and 302 and the inner surface of the one of the third and fourth electrodes 303 and 304 to the charger IC used to charge the battery of the electronic device 101 by controlling the switch included in the circuit of the electronic device 101. In this manner, the electronic device 101 may charge the battery with power received from the external device.

According to an embodiment of the disclosure, the electronic device 101 may connect at least a part of the electrodes 301, 302, 303 and 304 to at least one sensor of the electronic device 101 or the charger IC of the electronic device 101 by controlling the switch included in the circuit of the electronic device 101. For example, the electronic device 101 may determine whether the electronic device 101 has been worn on a part of a user's body through a grip sensor of the electronic device 101. If it is determined that the electronic device 101 has been worn on a part of a user's body, at least a part of the electrodes 301, 302, 303 and 304 may be connected to the at least one sensor of the electronic device 101 by controlling the switch. Further, if it is determined that the electronic device 101 has not been worn on a part of a user's body, at least a part of the electrodes 301, 302, 303 and 304 may be connected to the charger IC used to charge the battery of the electronic device 101 by controlling the switch. If the electronic device 101 determines that the residual power level of the battery is equal to or lower than a threshold, the electronic device 101 may connect at least a part of the electrodes 301, 302, 303 and 304 to the charger IC used to charge the battery of the electronic device 101 by controlling the switch. This operation is performed in order to place the electronic device 101 in a chargeable state by controlling the switch before the battery is consumed up.

According to an embodiment of the disclosure, the electronic device 101 may include at least one of the first sensor module 340 exposed from the first surface of the housing or the second sensor module 342 exposed from the second surface of the housing. The sensor modules 340 and 342 exposed from at least a part of the housing of the electronic device 101 may include the whole or a part of the sensor module 240 illustrated in FIG. 2. The sensor modules 340 and 342 may include at least one of an optical sensor or a semiconductor sensor. For example, the sensor modules 340 and 342 may include a pulse wave sensor that measures the pulses of the user. Further, the sensor modules 340 and 342 may include a heart rate monitor sensor that measures the heart rate of the user. The sensor modules 340 and 342 may include a sensor that measures at least one of the oxygen saturation (SpO2), blood pressure, or blood sugar of the user.

According to an embodiment of the disclosure, the electronic device 101 may include the display 360. The electronic device 101 may generate physical information or health information about the user based on a signal received through at least one of the electrodes 301, 302, 303, and 304 of the electronic device 101, and display the generated physical information or health information on the display 360 of the electronic device 101 or a display of the external device 102. Further, the electronic device 101 may charge the battery by means of at least one of the electrodes 301, 302, 303, and 304 of the electronic device 101, and display information related to the charging of the battery on the display 360 of the electronic device 101 or the display of the external device 102. The electronic device 101 may use at least one of the electrodes 301, 302, 303, and 304 of the electronic device 101 as a touch key that receives a user's touch input (e.g., a touch input or a drag input). The foregoing embodiments are exemplary, and the display 360 of the electronic device 101 may display a state of the electronic device 101, an execution screen of an application running in the electronic device 101, or information received from an external device in various manners. The electronic device 101 may provide the user with a part of signals generated in the electronic device 101 in various manners, for example, by light (LED), sound, or vibrations through an I/O interface of the electronic device 101 (e.g., the I/O interface illustrated in FIG. 1).

According to an embodiment of the disclosure, the electronic device 101 may include at least one groove 310 on a part of the housing. For example, the groove 310 may be formed into a cylinder, towards the inside of the electronic device 101 from outward. The groove 310 may not overlap with any electrode. For example, the groove 310 may be disposed between separately arranged electrodes.

When one surface of the electronic device 101 is brought into contact with one surface of an external device (e.g., the external device 102), the groove 310 may be provided to accommodate a protrusion member protruding from the surface of the external device. For example, the groove 310 may be engaged with the protrusion member protruding from the surface of the external device by accommodating the protrusion member. The electronic device 101 may receive at least one signal from the protrusion member of the external device engaged with the groove 310 through the groove 310. For this purpose, a terminal capable of receiving at least one external signal may be included in the groove 310. The electronic device 101 may identify whether the electronic device 101 is coupled to the external device based on at least one signal received through the groove 310. Further, the electronic device 101 may identify a direction of the coupling between the electronic device 101 and the external device based on at least one signal received through the groove 310.

According to another embodiment of the disclosure, instead of the electronic device 101, the external device (e.g., the external device 102) may identify whether the electronic device 101 is coupled to the external device. Further, instead of the electronic device 101, the external device may identify the direction of the coupling between the electronic device 101 and the external device. A specific embodiment related to the case where the identification takes place in the external device will be described later in detail with reference to FIGS. 10A, 10B and 10C.

According to an embodiment of the disclosure, the electronic device 101 may include a coupling member 350 connected to a part of the housing and configured to detachably couple the electronic device 101 to a part of a user's body. The coupling member 350 may include at least a part of the electrodes 301, 302, 303, and 304 or at least one sensor. The coupling member 350 may be electrically connected to a part of the housing of the electronic device 101 in order to transmit a signal received from the at least part of the electrodes 301, 302, 303, and 304 or the at least one sensor included in the coupling member 350 to the processor of the electronic device 101 (e.g., the processor 120 illustrated in FIG. 1 or the processor 210 illustrated in FIG. 2).

According to another embodiment of the disclosure, the electronic device 101 may analyze a signal received through the electrodes 301, 302, 303 and 304 by means of an external device (e.g., the external device 102). For example, the electronic device 101 may transmit a signal received through the electrodes 301, 302, 303 and 304 to the external device through a communication interface (e.g., the communication interface illustrated in FIG. 1) of the electronic device 101. The external device may analyze the signal received from the electronic device 101, and transmit analyzed information to the electronic device 101. The electronic device 101 may generate content corresponding to physical information or health information based on the information received from the external device. Further, the electronic device 101 may display the information received from the external device on the display 360 of the electronic device 101.

Figure 4:
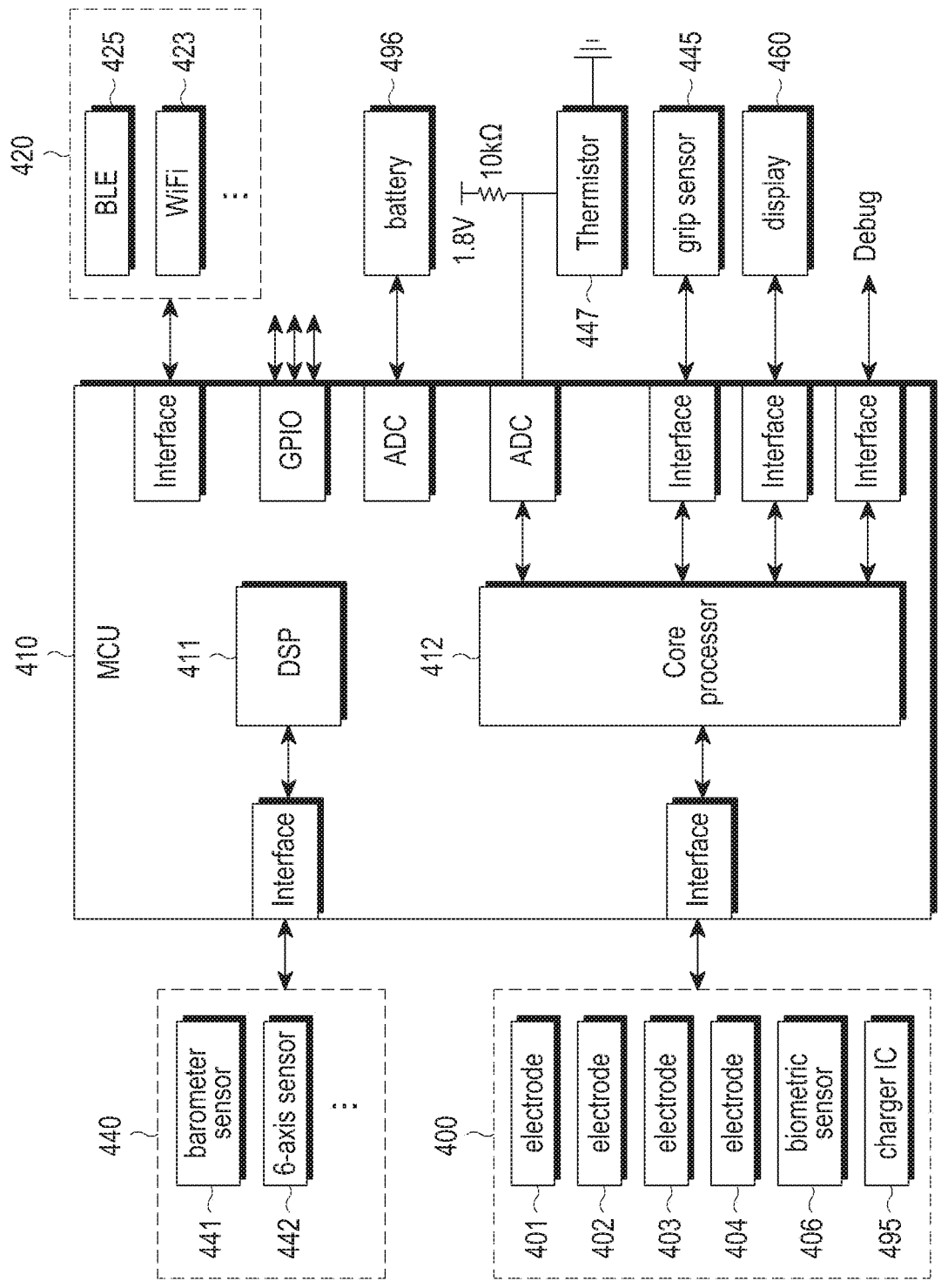
FIG. 4 is a block diagram illustrating an electronic device according to an embodiment of the disclosure.

FIG. 4 is a block diagram illustrating an electronic device according to an embodiment of the disclosure.

Referring to FIG. 4, an electronic device according to an embodiment may include at least a part of the components of the electronic device 101 illustrated in FIG. 1 or the electronic device 201 illustrated in FIG. 2, and a part of the components illustrated in FIG. 4 may correspond to at least a part of the components of the electronic device 101 illustrated in FIG. 1 or the electronic device 201 illustrated in FIG. 2.

Referring to FIG. 4, the electronic device 101 according to an embodiment of the disclosure may include a micro controller unit 410 (e.g., the processor 120 illustrated in FIG. 1 or the processor 210 illustrated in FIG. 2). The electronic device 101 may include at least a part of an electrode unit 400, a communication unit 420 (e.g., the communication interface 170 illustrated in FIG. 1 or the communication module 220 illustrated in FIG. 2), a sensor unit 440 (e.g., the sensor module 240 illustrated in FIG. 2), a display 460 (e.g., the display 160 illustrated in FIG. 1 or the display 260 illustrated in FIG. 2), and a battery 496 (e.g., the battery 296 illustrated in FIG. 2).

According to an embodiment of the disclosure, the micro controller unit 410 may include at least one processor and at least one interface. For example, the micro controller unit 410 may include at least one of a digital signal processor (DSP) 411 which may be used in computing a sensor algorithm, or a core processor 412 which may be used in driving an OS. According to another embodiment, the micro controller unit 410 may transmit a control signal to at least one of the components of the electronic device 101. The at least one component may be electrically connected to the micro controller unit 410 via at least one interface of the micro controller unit 410. As an interface that connects the micro controller unit 410 to the at least one component, at least one of an inter integrated circuit ($I^2C$), a serial programming interface (SPI), a universal asynchronous receiver/transmitter (UART), a general-purpose input/output (GPIO), or an ADC is available. Further, as an interface that connects the micro controller unit 410 to the at least one component, a serial interface, a synchronous transmission interface, or an asynchronous transmission interface may be used. According to various embodiments of the disclosure, an interface that connects at least two components to each other is not limited to the above embodiments, and as far as it is capable of connecting at least two components to each other, any interface is available.

According to an embodiment of the disclosure, the electrode unit 400 of the electronic device 101 may include at least one of electrodes 401, 402, 403, and 404, a biometric sensor 406, or a charger IC 495. The electrode unit 400 may be electrically connected to the micro controller unit 410 via at least one interface. For example, the electrode unit 400 may be electrically connected to the micro controller unit 410 via an SPI. Besides, the electrode unit 400 may be electrically connected to the micro controller unit 410 via various other I/O interfaces (e.g., the I/O interface 150 illustrated in FIG. 150). The electrode unit 400 may be configured to be controlled based on at least one control signal received from the micro controller unit 410.

According to another embodiment of the disclosure, the electrode unit 400 of the electronic device 101 may include at least one of the biometric sensor 406 or the charger IC 495, which is electrically (or conductively) connected to the electrodes 401, 402, 403, and 404.

The electrodes 401, 402, 403, and 404 may be exposed outwards from at least a part of the housing of the electronic device 101. The electronic device 101 may receive at least one signal through the electrodes 401, 402, 403, and 404. For example, if the electronic device 101 is coupled to a part of a user's body, the electronic device 101 may receive an electrical signal from the user through at least one of the electrodes 401, 402, 403, and 404. The electrical signal received through the electrodes 401, 402, 403, and 404 may be fine current flowing in the user's body. Further, if the electronic device 101 is connected to an external device (e.g., the external device 102) that supplies power, the electronic device 101 may receive power from the external device through the electrodes 401, 402, 403, and 404.

According to another embodiment of the disclosure, the electrode unit 400 may include at least one switch. The micro controller unit 410 of the electronic device 101 may control the at least one switch included in the electrode unit 400 based on at least one signal received through the electrodes 401, 402, 403, and 404. For example, if determining that the electronic device 101 is coupled to a part of the user's body, the micro controller unit 410 may electrically connect the electrodes 401, 402, 403, and 404 to the biometric sensor 406 by controlling the at least one switch included in the electrode unit 400 in order to acquire physical information or health information about the user. The biometric sensor 406 may generate the physical information or health information about the user based on at least one signal received from the electrodes 401, 402, 403, and 404.

If the electronic device 101 is connected to an external device (e.g., the external device 102) that supplies power, the micro controller unit 410 may electrically connect the electrodes 401, 402, 403, and 404 to the charger IC 495 by controlling the at least one switch included in the electrode unit 400 in order to charge the battery 496. The charger IC 495 may refer to a circuit capable of charging the battery 496 of the electronic device 101 with power received through the electrodes 401, 402, 403, and 404.

According to an embodiment of the disclosure, the communication unit 420 of the electronic device 101 may communicate an external device (e.g., the external device 102) and perform an over the air (OTA) connection operation by at least one of BLE 425, NFC, MST, or WiFi 423. Further, the communication unit 420 may include at least a part of the components of the communication interface 170 illustrated in FIG. 1 or the components of the communication module 220 illustrated in FIG. 2. The communication unit 420 and the micro controller unit 410 may be connected electrically to each other via at least one interface. For example, the communication unit 420 and the micro controller unit 410 may be connected electrically by a UART. The communication unit 420 and the micro controller unit 410 may be connected electrically via various other I/O interfaces (e.g., the I/O interface 150 illustrated in FIG. 1). The communication unit 420 may be configured to be controlled based on at least one control signal received from the micro controller unit 410. Further, the communication unit 420 may be used to connect the electronic device 101 to the external device by cable or wirelessly.

According to an embodiment of the disclosure, the sensor unit 440 of the electronic device 101 may include at least one of a barometer sensor 441 or a 6-axis sensor 442. The sensor unit 440 of the electronic device 101 may include a motion sensor based on a micro electro mechanical system. The sensor unit 440 may include at least a part of the components of the sensor module 240 illustrated in FIG. 2. The sensor unit 440 may be electrically connected to the micro controller unit 410 via at least one interface. For example, the sensor unit 440 may be electrically connected to the micro controller unit 410 via an I$^2$C. The sensor unit 440 may be electrically connected to the micro controller unit 410 via various I/O interfaces (e.g., the I/O interface 150 illustrated in FIG. 1). The sensor unit 440 may be configured to be controlled based on at least one control signal received from the micro controller unit 410.

At least one sensor included in the sensor unit 440 may be provided inside the electronic device 101 or exposed outwards through at least a part of the housing of the electronic device 101. For example, the barometer sensor 441 included in the sensor unit 440 may be provided inside the electronic device 101, for use in measuring the altitude of the electronic device 101. The 6-axis sensor 442 included in the sensor unit 440 may be provided inside the electronic device 101, for use in identifying a motion of the electronic device 101. An optical sensor (not shown) which may be included in the sensor unit 440 may be provided in at least a part of the housing of the electronic device 101, for use in measuring at least one of the oxygen saturation (SpO2), blood pressure, blood sugar, or heart rate of the user.

According to an embodiment of the disclosure, the electronic device 101 may include at least one of a grip sensor 445 or a thermistor 447. The micro controller unit 410 may determine whether the electronic device 101 is coupled to a body based on information acquired through the grip sensor 445. For example, the grip sensor 445 may sense a capacitance variation caused by an object located within a predetermined distance from the electronic device 101. According to another embodiment, the grip sensor 445 may be replaced with a capacitive touch sensor. The micro controller unit 410 may measure the dielectric constant of the object around the electronic device 101 based on the capacitance variation sensed by the grip sensor 445. The micro controller unit 410 may determine whether the electronic device 101 is coupled to the body based on the measured dielectric constant. The grip sensor 445 may be electrically connected to the micro controller unit 410 via an I$^2$C. The grip sensor 445 may be electrically connected to the micro controller unit 410 via various I/O interfaces (e.g., the I/O interface 150 illustrated in FIG. 1).

According to another embodiment of the disclosure, the micro controller unit 410 may determine whether the electronic device 101 is coupled to a body based on information acquired through the thermistor 447. For example, the micro controller unit 410 may measure the temperature of an object contacting the electronic device 101 through the thermistor 447. The micro controller unit 410 may determine whether the electronic device 101 is coupled to the body based on the measured temperature. The thermistor 447 may be electrically connected to the micro controller unit 410 via an ADC. The thermistor 447 may be electrically connected to the micro controller unit 410 via various I/O interfaces (e.g., the I/O interface 150 illustrated in FIG. 1).

According to an embodiment of the disclosure, the electronic device 101 may include the display 460. The micro controller unit 410 may display, on the display 460, information acquired through at least one of the components of the electronic device 101 such as the electrode unit 400, the communication unit 420, or the sensor unit 440. For this purpose, the display 460 may be electrically connected to the micro controller unit 410 via at least one interface. For example, the display 460 may be electrically connected to the micro controller unit 410 via an I$^2$C. The display 460 may be electrically connected to the micro controller unit 410 via various serial or parallel I/O interfaces (e.g., the I/O interface 150 illustrated in FIG. 1). The display 460 may be configured to be controlled based on at least one control signal received from the micro controller unit 410.

According to an embodiment of the disclosure, the micro controller unit 410 of the electronic device 101 may exchange data with an external object via at least one interface of the micro controller unit 410. For example, the micro controller unit 410 may exchange data with the external object via a GPIO. According to another embodiment, at least one of UARTs or at least one of I$^2$Cs in the micro controller unit 410 may be a field programmable gate array (FPGA), and include a semiconductor device including a designable logic device and a programmable internal line. For example, at least one of the UARTs of the micro controller unit 410 may be an FPGA, for use in debugging. Further, at least one of the I$^2$Cs of the micro controller unit 410 may be an FPGA connectable to the display 460. The interfaces described in the disclosure are merely examples for connecting at least two components to each other, not limiting the configuration of the disclosure. The interfaces described in the disclosure may be replaced with other compatible interfaces.

Figure 5:
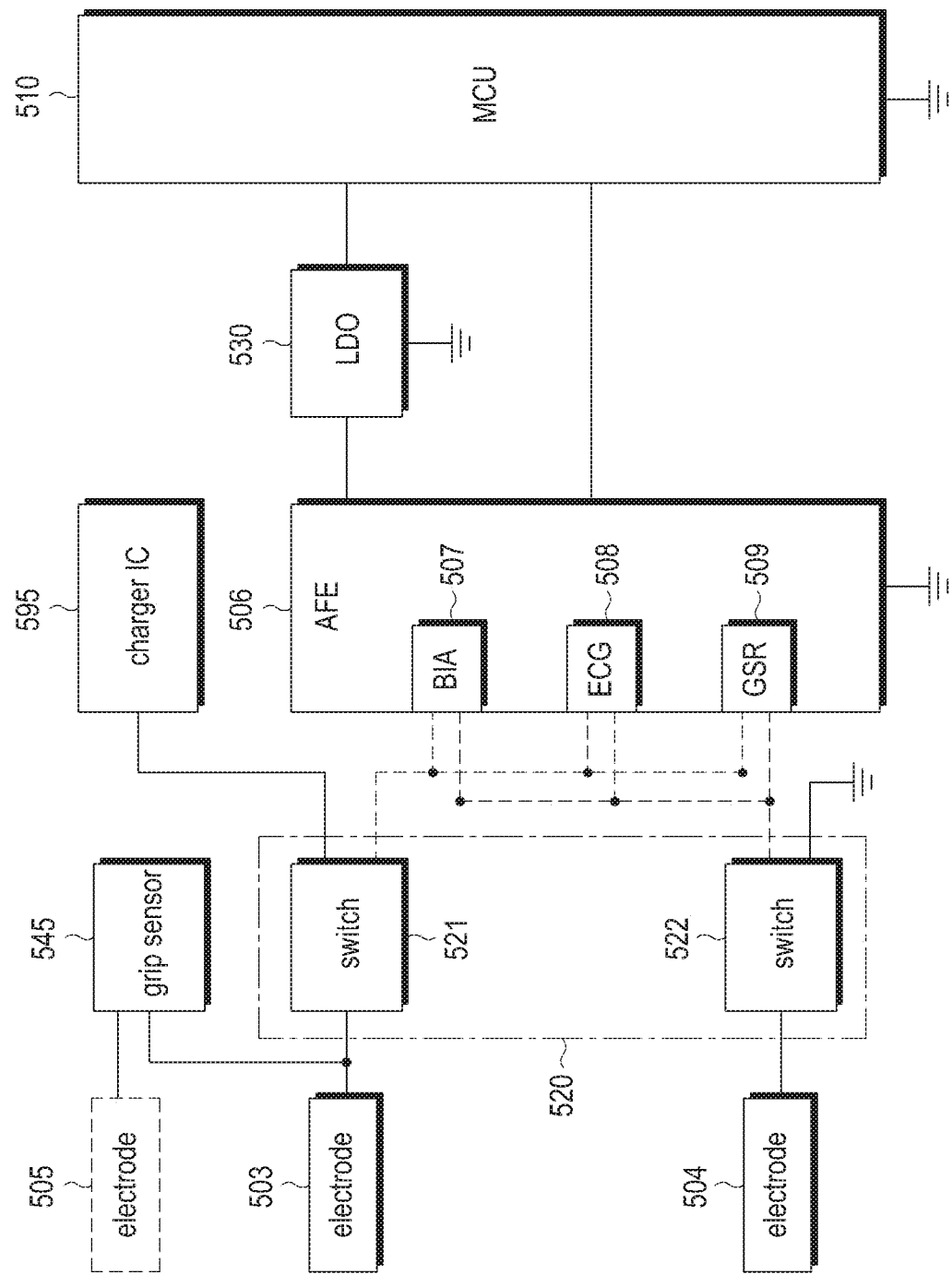
FIG. 5 is block diagram illustrating an electrode unit according to an embodiment of the disclosure.

FIG. 5 is a block diagram illustrating an electrode unit according to an embodiment of the disclosure.

Referring to FIG. 5, the electronic device 101 may include a micro controller unit 510 (e.g., the processor 120 illustrated in FIG. 1 or the processor 210 illustrated in FIG. 2). The electronic device 101 may include at least one of electrodes 503 and 504, a switch unit 520, at least one biometric sensor 507, 508, and 509, or a charger IC 595.

According to an embodiment of the disclosure, the micro controller unit 510 may be electrically connected to an AFE 506 which may be used in processing a biometric signal. The AFE 506 may include at least one biometric sensor. For example, the AFE 506 may include at least one of a BIA sensor 507 for measuring the body fat rate of the user, an ECG sensor 508 for measuring the ECG of the user, or a GSR sensor 509 for measuring the skin resistance of the user. The at least one biometric sensor included in the AFE 506 may generate physical information or health information about the user, using at least one signal received through the electrodes 503 and 504. The electronic device 101 may include a low voltage drop out (LDO) 530 for supplying power of a predetermined voltage irrespective of a change in the voltage or frequency of input power, as a device for stably supplying power to each component.

According to an embodiment of the disclosure, the electrodes 503 and 504 may be exposed outwards through at least a part of the housing of the electronic device 101. Accordingly, when the electronic device 101 is coupled to the user's body, at least one of the fifth electrode 503 or the sixth electrode 504 may contact at least a part of the user's body. The electronic device 101 may receive at least one signal related to the user through the electrode contacting the at least part of the user's body. Further, at least one of the fifth electrode 503 or the sixth electrode 504 may contact a conductive terminal of an external device (e.g., the external device 102). The electronic device 101 may receive at least one signal from the external device through the electrode contacting the conductive terminal of the external device, or transmit at least one signal to the external device through the electrode contacting the conductive terminal of the external device. The fifth electrode 503 and the sixth electrode 504 may be two of the first electrode 301, the second electrode 302, the third electrode 303, and the fourth electrode 304 illustrated in FIG. 3.

According to an embodiment of the disclosure, the electronic device 101 may include a grip sensor 545. The micro controller unit 510 may determine whether the electronic device 101 is coupled to the user's body, through the grip sensor 545. For example, the grip sensor 545 may sense whether the electronic device 101 is coupled to the user's body, based on a signal received through the fifth electrode 503 exposed outwards. The micro controller unit 510 may determine whether the electronic device 101 is coupled to the user's body, using a result sensed through the grip sensor 545. According to another embodiment, the sixth electrode 504 may also be connected to the grip sensor 545, for use in determining whether the electronic device 101 is coupled to the user's body. According to another embodiment, the grip sensor 545 may be connected to an electrode 505 other than the fifth electrode 503 and the sixth electrode 504, for use in determining whether the electronic device 101 is coupled to the user's body. For example, the electrode 505 may be provided inside the electronic device 101, without being exposed outwards through the housing of the electronic device 101.

If determining that the electronic device 101 is coupled to the user's body, the micro controller unit 510 may electrically connect the fifth electrode 503 and the sixth electrode 504 to the at least one biometric sensor 507, 508, and 509 of the AFE 506 by controlling switches 521 and 522. The at least one biometric sensor of the AFE 506 may generate physical information or health information about the user based on at least one signal received through the fifth electrode 503 and the sixth electrode 504. For example, the BIA sensor 507 may measure the body fat rate of the user, based on at least one signal received through the fifth electrode 503 and the sixth electrode 504, and transmit the measurement result to the micro controller unit 510. The ECG sensor 508 may measure the ECG of the user based on at least one signal received through the fifth electrode 503 and the sixth electrode 504, and transmit the measurement result to the micro controller unit 510. The GSR sensor 509 may measure the skin resistance of the user based on at least one signal received through the fifth electrode 503 and the sixth electrode 504, and transmit the measurement result to the micro controller unit 510. The measured skin resistance may be used to determine a stress level that the user feels.

If determining that the electronic device 101 is not coupled to the user's body, the micro controller unit 510 may electrically connect the fifth electrode 503 to the charger IC 595, while grounding the sixth electrode 504, by controlling the switches 521 and 522. If determining that the residual battery power level of the electronic device 101 is equal to or lower than a threshold, the micro controller unit 510 may electrically connect the fifth electrode 503 to the charger IC 595, while grounding the sixth electrode 504, by controlling the switches 521 and 522. The micro controller unit 510 may charge the battery of the electronic device 101, using a potential difference between the fifth electrode 503 and the sixth electrode 504. According to another embodiment, the micro controller unit 510 may electrically connect the sixth electrode 504 to the charger IC 595, while grounding the fifth electrode 503.

According to an embodiment of the disclosure, the micro controller unit 510 may check a motion of the electronic device 101, even though determining that the electronic device 101 is not coupled to the user's body. For example, it may occur the electronic device 101 is not coupled to the user's body temporarily (e.g., a coupling member (e.g., the coupling member 350) of the electronic device 101 is temporarily loose), which may be additionally considered by the micro controller unit 510. For example, if determining through the grip sensor 545 or the electrode 503 or 504 that the electronic device 101 is not coupled to the user's body, the micro controller unit 510 may determine whether the electronic device 101 is temporarily not coupled to the user's body by additionally checking state information related to the electronic device 101 (e.g., a motion of the electronic device 101). According to another embodiment, if determining that a part of the user's body is located within a predetermined distance (a hovering state) through the grip sensor 545, the micro controller unit 510 may control an electrical connection state between the electronic device 101 and the charger IC 595.

According to an embodiment of the disclosure, the electronic device 101 may further include a voltage sensing circuit (not shown). The voltage sensing circuit may determine whether a voltage received through the electrode 503 or 504 of the electronic device 101 is equal to or larger than a predetermined threshold, or whether the voltage is larger than the threshold. For example, if sensing a predetermined voltage 5V through the voltage sensing circuit, the electronic device 101 may connect the electrode 503 or 504 to the charger IC 595 by controlling the switch 521 or 522.

According to an embodiment of the disclosure, the electronic device 101 may include the switch unit 520 to change an object to be connected to the electrodes 503 and 504 according to a state of the electronic device 101 or the type of an object coupled to the electronic device 101. The switch unit 520 may include at least one switch, and when needed, a plurality of switches. For example, the switch unit 520 may include the first switch 521 and the second switch 522.

Figure 6:
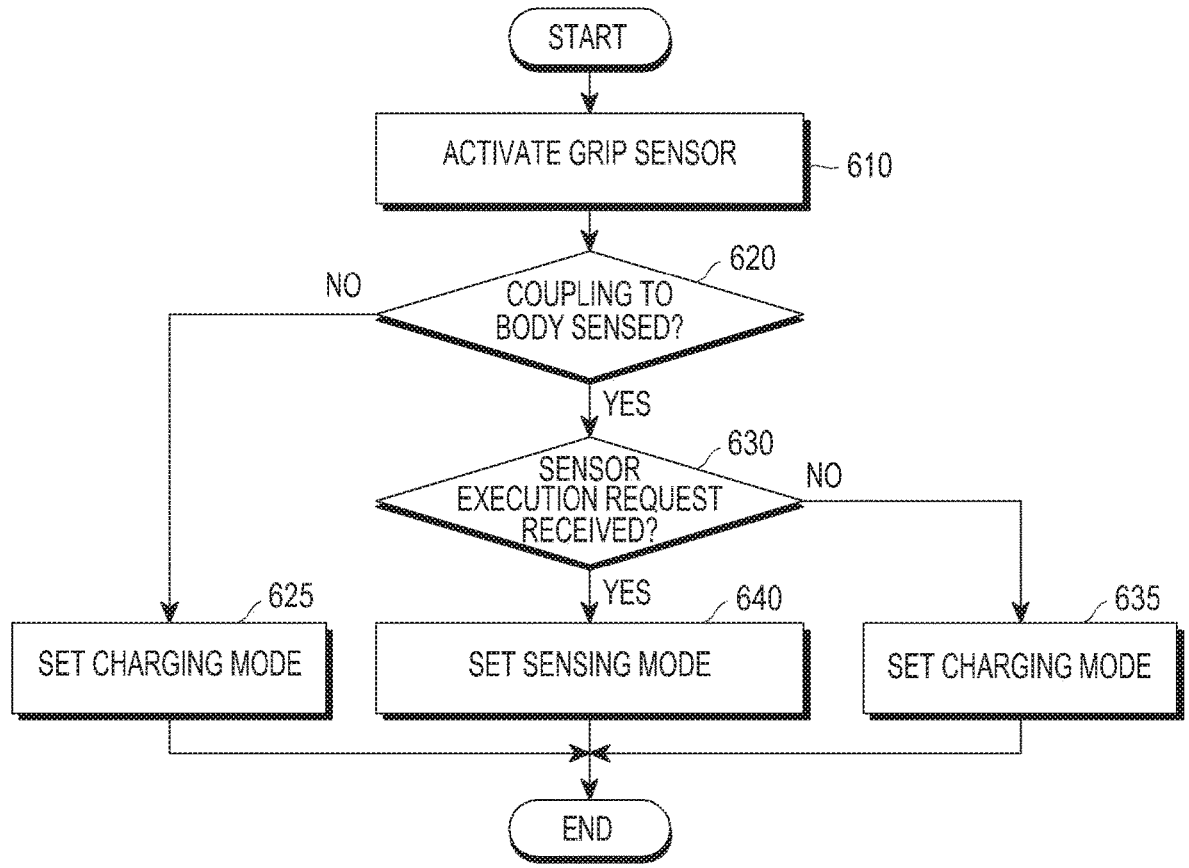
FIG. 6 is a flowchart illustrating a method for determining a mode of an electronic device according to an embodiment of the disclosure.

FIG. 6 is a flowchart illustrating a method for determining a mode of an electronic device according to an embodiment of the disclosure.

An entity that performs the method may be a processor (e.g., the processor 120 illustrated in FIG. 1 or the processor 210 illustrated in FIG. 2) in an electronic device (e.g., the electronic device 101 illustrated in FIG. 1 or the electronic device 201 illustrated in FIG. 2) including at least one electrode (e.g., the electrodes 301, 302, 303, and 304 illustrated in FIG. 3), at least one sensor (e.g., the sensor module 240 illustrated in FIG. 2), and the processor (e.g., the processor 120 illustrated in FIG. 1 or the processor 210 illustrated in FIG. 2).

Referring to FIG. 6, the electronic device 101 may be powered on in operation 610. The processor 120 may activate the grip sensor included in the electronic device 101 in response to the power-on of the electronic device 101. The processor 120 may activate the grip sensor included in the electronic device 101 in response to sensing of a motion or state change of the electronic device 101 through at least one sensor included in the electronic device 101.

In operation 620, the processor 120 may determine whether the electronic device 101 is coupled to a body. For example, the grip sensor may sense a capacitance variation caused by an object within a predetermined distance from the electronic device 101. The processor 120 may measure the dielectric constant of the object around the electronic device 101 based on the capacitance variation sensed by the grip sensor. The processor 120 may determine whether the electronic device 101 is coupled to the body, based on the measured dielectric constant. If determining that the electronic device 101 is coupled to the body, the processor 120 may perform operation 630.

In operation 630, the processor 120 may determine whether a request related to execution of at least one sensor of the electronic device 101 has been received. The processor 120 may receive a request related to execution of the biometric sensor using a signal received through an electrode. For example, the processor 120 may receive a request related to measurement of the body fat rate of the user, a request related to measurement of the ECG of the user, or a request related to measurement of the stress index of the user. This request may mean execution of an application including a function for measuring at least one of the body fat rate, ECG, or skin resistance of the user. If determining that the biometric sensor using an electrode needs to be executed, the processor 120 may perform operation 640.

In operation 640, the processor 120 may set the electronic device 101 to a sensing mode. For example, the processor 120 may electrically connect the electrode to the biometric sensor by controlling the switch included in the circuit of the electronic device 101. In this manner, upon completion of setting the sensing mode by electrically connecting the electrode to the biometric sensor, the biometric sensor may generate physical information or health information about the user, using at least one signal received through the electrode. If determining that the electronic device 101 is coupled to the body in operation 620, the processor 120 may set the electronic device 101 to the sensing mode even without receiving a sensor execution request in operation 630. Once the electronic device 101 is coupled to the body, the processor 120 may activate the biometric sensor using the electrode. However, if determining that the residual battery power level of the electronic device 101 is equal to or lower than a threshold, the processor 120 may electrically connect the electrode to the charger IC by controlling the switch included in the circuit of the electronic device 101. This operation is performed to place the electronic device 101 in a chargeable state by controlling the switch before the battery is consumed up.

If determining that the electronic device 101 is not coupled to the body in operation 620, the processor 120 may perform operation 625. For example, the electrode of the electronic device 101 may be configured to be connected to the charger IC by default. Unless a predetermined condition is satisfied, the processor 120 may maintain a charging mode in which the electrode is electrically connected to the charger IC by controlling the switch included in the circuit of the electronic device 101.

If a request related to execution of the biometric sensor using the electrode has not been received in operation 630, the processor 120 may perform operation 635. For example, if the request related to execution of the biometric sensor using the electrode has not been received, the processor 120 may maintain the default mode being the charging mode by controlling the switch included in the circuit of the electronic device 101.

In the above embodiment, use of the grip sensor is exemplary, and the grip sensor may be replaced with any other sensor as far as it is capable of sensing whether the electronic device 101 has contacted a part of a user's body or is coupled to a part of the user's body.

Figure 7A:
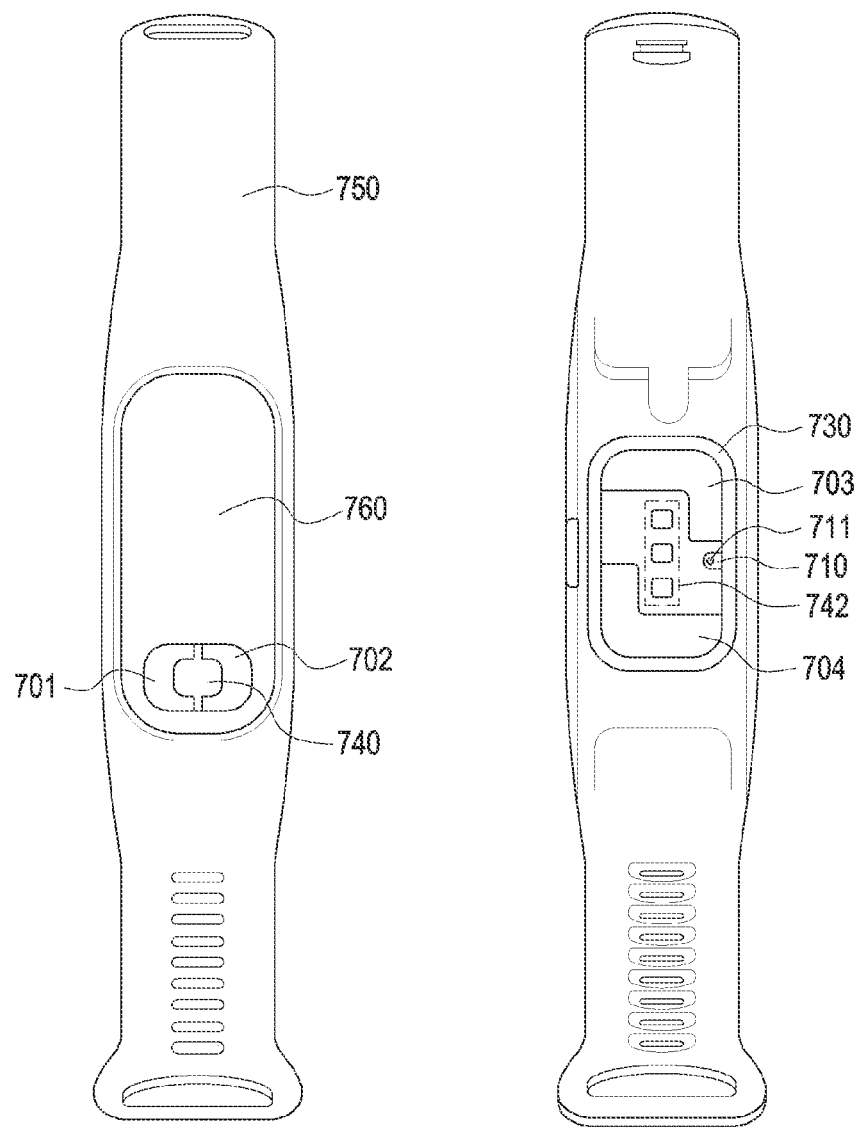
FIGS. 7A and 7B are views illustrating a structure of an electronic device according to various embodiments of the disclosure.
Figure 7B:
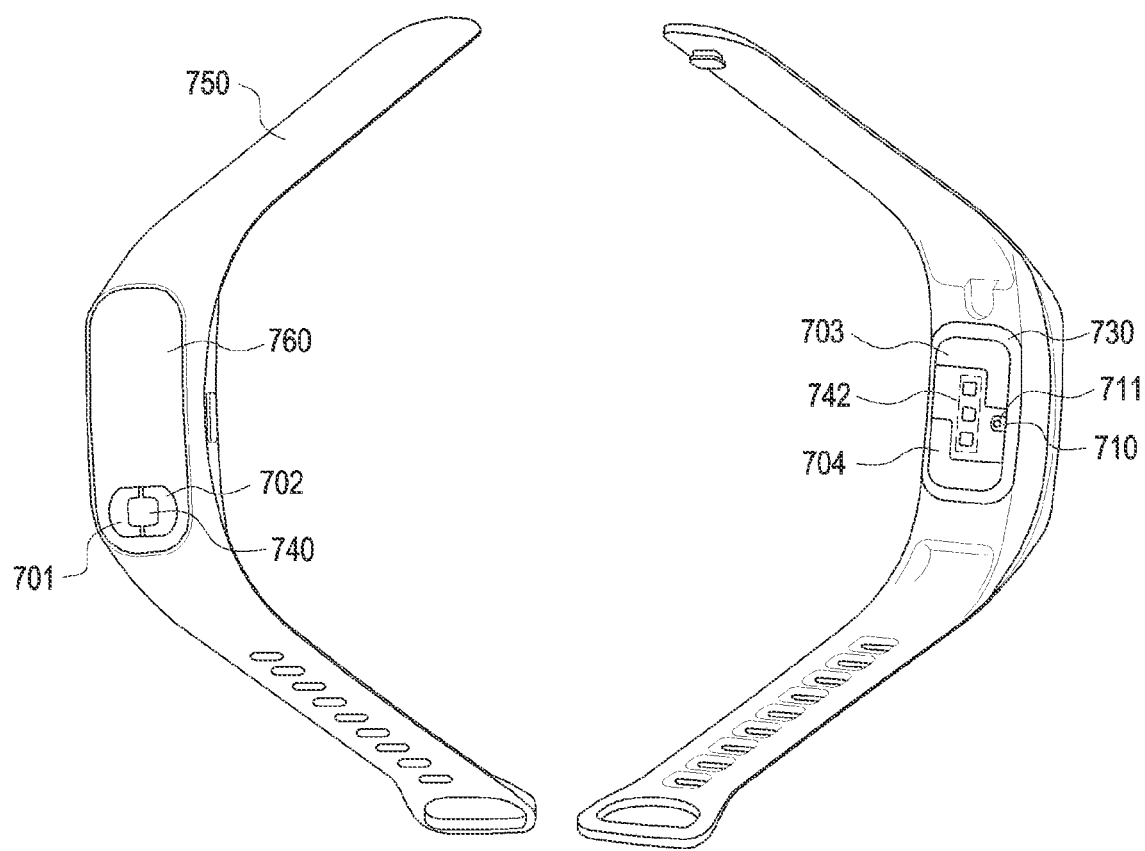

FIGS. 7A and 7B are views illustrating the structure of an electronic device according to various embodiments of the disclosure.

FIG. 7A illustrates front and rear views of the electronic device, and FIG. 7B illustrates side views of the electronic device. A first electrode 701, a second electrode 702, a first sensor module 740, and a display 760 may be mounted on a first surface of a housing of the electronic device 101, for example, the front surface of the housing of the electronic device 101. The first electrode 701 and the second electrode 702 may be shaped into "U", surrounding the first sensor module 740. However, the shapes or sizes of the first electrode 701 and the second electrode 702 are not limited thereto. The first sensor module 740 may be exposed outwards from the front surface of the housing of the electronic device 101. The display 760 may display information acquired from components of the electronic device 101. The display 760 may include a touch panel, and the touch panel may be used as an input interface for receiving a touch input of the user. The electronic device 101 may include a coupling member 750 which is connected to a part of a body with the display 760 and so on mounted thereon and which is configured to couple the electronic device 101 detachably to a part of the user's body. The coupling member 750 may include at least one connection part so that the electronic device 101 may be coupled to a part of the user's body. Further, the coupling member 750 may be configured in the form of an elastic band. According to another embodiment, at least one electrode or at least one sensor module may be mounted in a part of the coupling member 750.

A third electrode 703, a fourth electrode 704, a second sensor module 742, and at least one groove 710 may be provided on a second surface of the housing of the electronic device 101, for example, the rear surface of the housing of the electronic device 101. The third electrode 703 and the fourth electrode 704 may be disposed along the periphery of the second sensor module 742, and shaped symmetrically into "L". However, the shapes or sizes of the third electrode 703 and the fourth electrode 704 are not limited thereto. The second sensor module 742 may be exposed outwards from the rear surface of the housing of the electronic device 101. The second sensor module 742 may be a module including an optical sensor, covered with a transparent (or semi-transparent) material so that light may pass therethrough. In this case, the second sensor module 742 may not be exposed outwards directly from the rear surface of the housing. If the electronic device 101 is coupled to a part of the user's body, the rear surface of the electronic device may contact a part of the user's wrist. The third electrode 703, the fourth electrode 704, and the second sensor module 742 may receive at least one signal from the contacting part of the user's wrist, and generate physical information or health information about the user based on the received signal.

The third electrode 703, the fourth electrode 704, the second sensor module 742, and the at least one groove 710 may be disposed in a protruding area 730 of the rear surface of the electronic device 101. When the electronic device 101 is coupled to the user's body, the protruding area 730 of the rear surface of the electronic device 101 may help the electrodes 703 and 704 or the second sensor module 742 of the electronic device 101 in the protruding area 730 to contact a part of the user's body.

The at least one groove 710 may be configured in the form of a cylinder, towards the inside of the electronic device 101 from outward. Since the at least one groove 710 is recessed towards the inside of the electronic device 101, when the electronic device 101 is coupled to an external device (e.g., the external device 102) through the rear surface of the electronic device 101, the at least one groove 710 may accommodate at least one protrusion member protruding from a coupling surface of the external device. According to an embodiment, only one groove 710 may be provided on the rear surface of the electronic device 101. If the electronic device 101 is coupled to the external device through the rear surface of the electronic device 101, the processor 120 may determine a direction in which the electronic device 101 is coupled to the external device by identifying a protrusion member of the external device accommodated in the groove 710. For example, if the electronic device 101 is coupled to the external device in a first direction, a first protrusion member among protrusion members protruding from a coupling surface of the external device may be accommodated in the groove 710. The processor 120 may determine that the electronic device 101 is coupled to the external device in the first direction by identifying the first protrusion member accommodated in the groove 710. In this manner, the processor 120 may determine that the electronic device 101 is coupled to the external device in a second direction by identifying a second protrusion member accommodated in the groove 710. At least one protrusion member may be provided in at least a part of the housing of the electronic device, and an accommodation part such as the groove 710 may be provided on a part of the coupling surface of the external device (e.g., the external device 102).

According to an embodiment of the disclosure, a terminal 711 (e.g., an electrode or a sensor) that may determine whether a protrusion member of an external device (e.g., the external device 102) has been accommodated in the groove 710 may further be provided in the groove 710 of the electronic device 101. The processor 120 of the electronic device 101 may determine whether the protrusion member of the external device has been accommodated in the groove 710 by means of the terminal 711 provided in the groove 710. For example, if contact between the protrusion member of the external device and the terminal 711 provided in the groove 710 of the electronic device 101 is sensed, the processor 120 may identify whether the electronic device 101 is coupled to the external device and a direction in which the electronic device 101 is coupled to the external device.

According to another embodiment of the disclosure, the external device coupled to the electronic device 101 may be a charger capable of supplying power. The electronic device 101 may control the switch included in the circuit of the electronic device 101 according to a direction in which the electronic device 101 is coupled to the charger. For example, the processor 120 may control the switch included in the circuit of the electronic device 101 in order to match the polarity of power received through each of the third and fourth electrodes 703 and 704 to the polarity of the charger IC. If the electronic device 101 is coupled to the charger in the first direction, the third electrode 703 may be connected to a 5-V terminal of the charger, whereas the fourth electrode 704 may be connected to a grounding terminal of the charger. In this case, the processor 120 may control the switch included in the circuit of the electronic device 101 so that the third electrode 703 may be connected to an input terminal of the charger IC, and the fourth electrode 704 may be connected to a grounding terminal inside the electronic device 101. Further, if the electronic device 101 is coupled to the charger in the second direction, the third electrode 703 may be connected to the grounding terminal of the charger, whereas the fourth electrode 704 may be connected to the 5-V terminal of the charger. In this case, the processor 120 may control the switch included in the circuit of the electronic device 101 so that the third electrode 703 may be connected to the grounding terminal inside the electronic device 101, and the fourth electrode 704 may be connected to the input terminal of the charger IC.

The embodiments described with reference to FIGS. 7A and 7B are merely examples of various embodiments of the disclosure, and the electronic device 101 may be controlled in a different manner from in the foregoing embodiments according to the type of a charger.

Figure 8A:
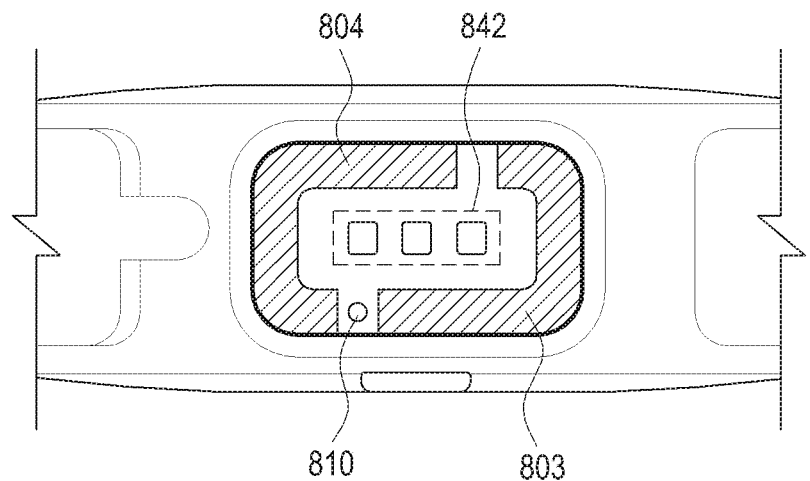
FIGS. 8A, 8B and 8C are views illustrating a structure of an electrode unit according to various embodiments of the disclosure.
Figure 8B:
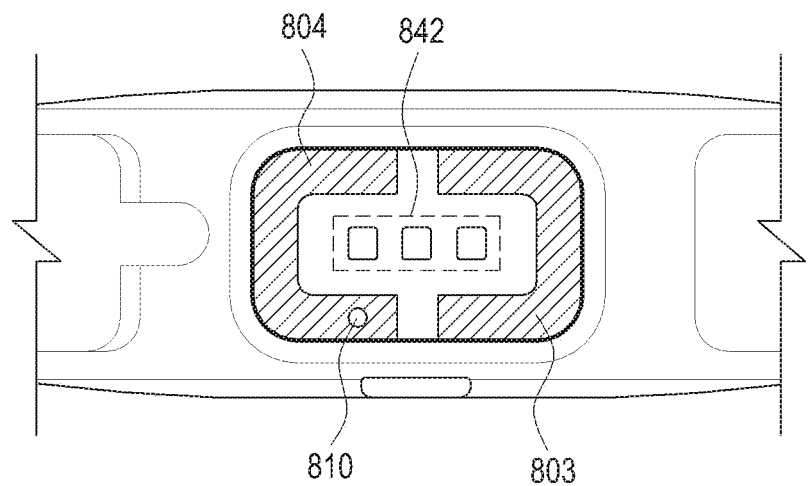
Figure 8C:
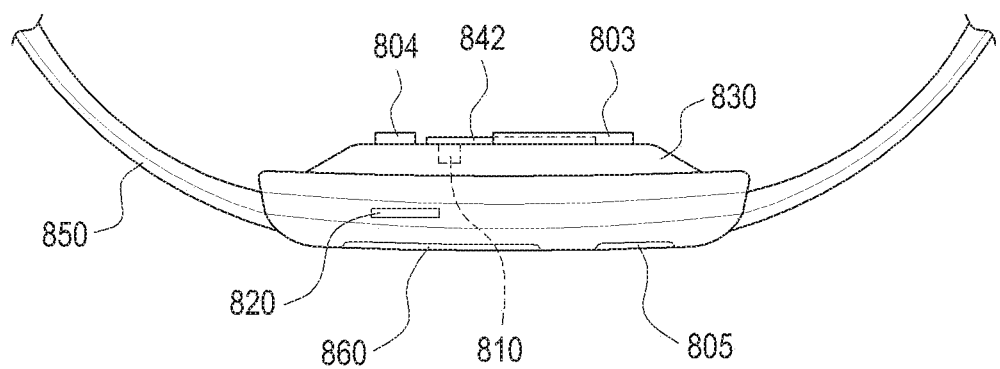

FIGS. 8A, 8B and 8C are views illustrating the structure of an electrode unit according to various embodiments of the disclosure.

Referring to FIGS. 8A, 8B and 8C, the electronic device 101 may include electrodes 803 and 804, at least one sensor module 842, and a groove 810.

According to an embodiment of the disclosure, the electronic device 101 may include at least one electrode (e.g., the electrodes 301, 302, 303, and 304) exposed through at least one of the surfaces of a housing of the electronic device 101. For example, the electronic device 101 may include the third electrode 803 and the fourth electrode 804 exposed through at least a part of the rear surface of the housing of the electronic device 101. The third electrode 803 and the fourth electrode 804 may be configured to be symmetrical. Each of the third electrode 803 and the fourth electrode 804 may include a first part extended to a first length, a second part extended to a second length from a first end of the first part at the right angle with the first part, and a third part extended to a third length from a second end of the first part in parallel to the second part. The first part, the second part, and third part may be an electrically and physically connected structure or a structure formed by bending one conductive member. The first, second, and third lengths may be different according to a design, and at least two of the first, second, and third lengths may be equal.

Referring to FIG. 8A, the third electrode 803 and the fourth electrode 804 may be disposed along the periphery of the at least one sensor module 842, and may be shaped symmetrically into "J". The third electrode 803 and the fourth electrode 804 may be arranged symmetrically to acquire a more accurate measurement result in checking physical information or health information about the user. Further, the third electrode 803 and the fourth electrode 804 may be spaced from each other by a predetermined distance or more in order to prevent short circuit during charging the battery of the electronic device 101. The at least one sensor module 842 or the groove 810 may be interposed between the third electrode 803 and the fourth electrode 804. The groove 810 may be positioned in an area with no electrode arranged therein in a protrusion unit (e.g., the protruding area 730) of the rear surface of the electronic device 101, and the position of the groove 810 may vary with the shapes of the electrodes.

Referring to FIG. 8B, the third electrode 803 and the fourth electrode 804 may be disposed along the periphery of the at least sensor module 842, and shaped symmetrically into "U". Similarly to the foregoing embodiment, the third electrode 803 and the fourth electrode 804 may be arranged symmetrically in order to acquire a more accurate measurement result in checking physical information or health information about the user. The third electrode 803 and the fourth electrode 804 may be spaced from each other by a predetermined distance or more to prevent short circuit during charging the battery of the electronic device 101. The groove 810 may be disposed in at least a part of the third electrode 803 and the fourth electrode 804, and the at least one sensor module 842 may be interposed between the third electrode 803 and the fourth electrode 804.

FIG. 8C is a view seen from a side of an electronic device. The electronic device may include at least one electrode 805, a display 860, and at least one sensor module (not shown) on a first surface of a housing, for example, the front surface of the housing. The electronic device may include the third electrode 803, the fourth electrode 804, the second sensor module 842, and the at least one groove 810 on a second surface of the housing, for example, the rear surface of the housing. The third electrode 803, the fourth electrode 804, the second sensor module 842, and the at least one groove 810 may be provided in a protruding area 830 of the rear surface of the electronic device. The electronic device may include at least one button 820 on a third surface of the housing, for example, a side surface of the housing. The electronic device may be connected to an at least one coupling member 850 through a fourth surface of the housing.

Figure 9:
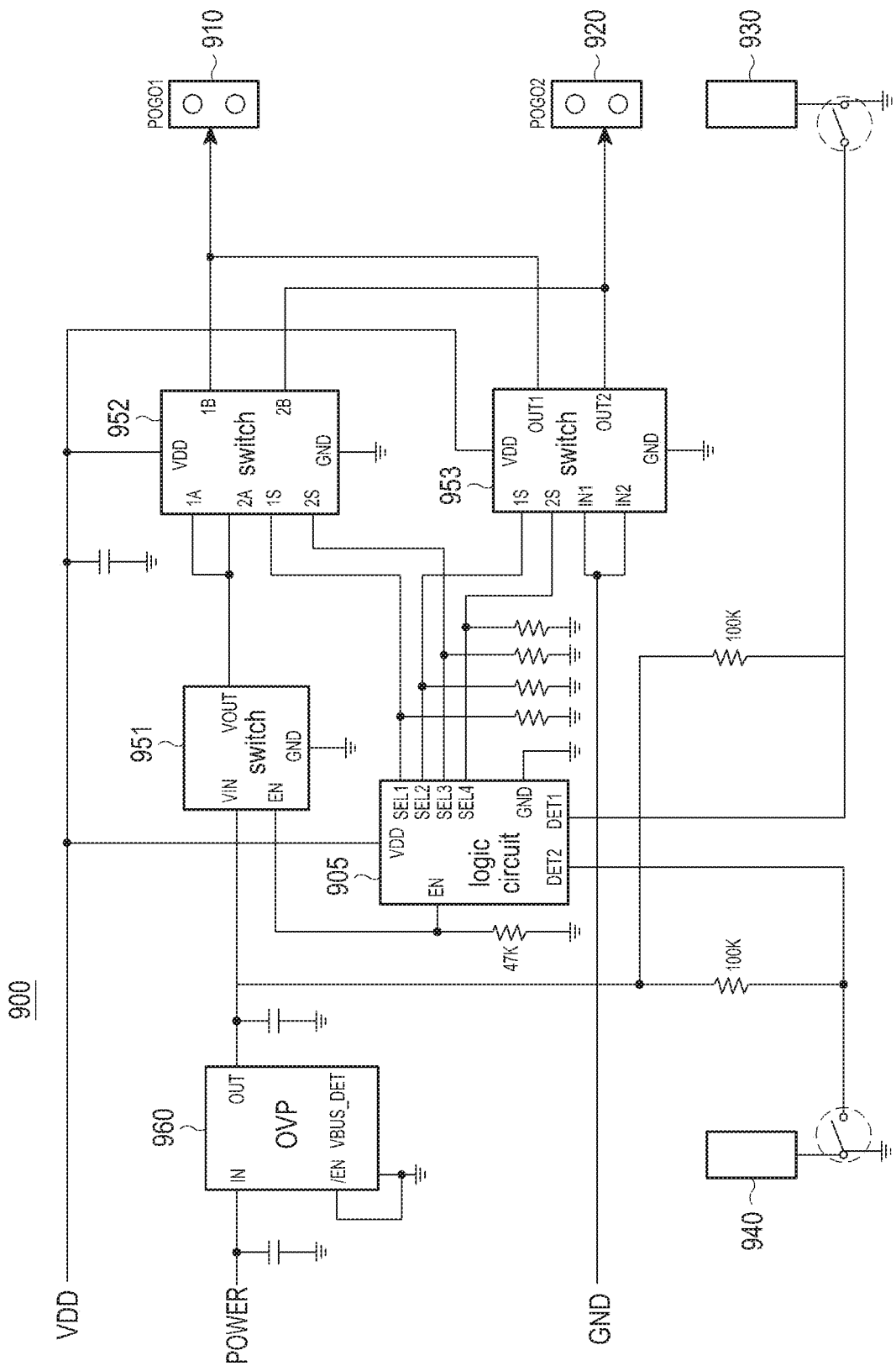
FIG. 9 is a circuit diagram illustrating a charger according to an embodiment of the disclosure.

FIG. 9 is a circuit diagram of a charger 900 according to an embodiment of the disclosure.

Referring to FIG. 9, the charger 900 according to an embodiment of the disclosure may include at least one of a logic circuit 905, charging terminals 910 and 920, sensing terminals 930 and 940, switches 951, 952 and 953, or an over-voltage protector (OVP) 960. The charger 910 may also include a power management module (e.g., the power management module 295 illustrated in FIG. 2).

According to an embodiment of the disclosure, the charger 900 may be provided with the OVP 960 to thereby protect a circuit from over-voltage. For example, if a voltage higher than a rated I/O voltage of the charger 900 is applied to the OVP 960, the OVP 960 may ground a part of terminals to protect components inside the charger 900. A voltage output from the OVP 960 may be applied to the logic circuit 900 and the switches 952 and 953, and thus operate each component. The voltage output from the OVP 960 may be applied to the switch 952 through the switch 951, and thus used as an output voltage of the charger 900. A voltage output from the OVP 960 may be used as a power voltage VDD for circuits included in the charger 910.

According to an embodiment of the disclosure, the charger 900 may further include a converter (not shown) for converting the voltage of input power. An output voltage of the converter may be applied to the switch 952 through the switch 951 and used as an output voltage of the charger 900.

According to an embodiment of the disclosure, the charging terminals 910 and 920, and the sensing terminals 930 and 940 may be exposed outwards through at least one surface of a housing of the charger 900. When the charger 900 is coupled to an electronic device (e.g., the electronic device 101 illustrated in FIG. 1 or the electronic device 201 illustrated in FIG. 2), the charging terminals 910 and 920 may contact an electrode (e.g., the electrodes 301, 302, 303, and 304 illustrated in FIG. 3) of the electronic device 101. When the charger 900 is coupled to the electronic device, the sensing terminals 930 and 940 may be accommodated in a groove (e.g., the groove 310 illustrated in FIG. 3) of the electronic device 101 or contact a part of the housing of the electronic device 101.

When the charger 900 is coupled to the electronic device, the charging terminals 910 and 920 may contact the electrode of the electronic device 101. When the charger 900 is coupled to the electronic device, the sensing terminals 930 and 940 may be accommodated in the groove of the electronic device 101 or contact a part of the housing of the electronic device 101. Each of the charging terminals 910 and 920, and the sensing terminals 930 and 940 may be configured as a cylindrical conductive member having a spring inside and two pins protruding in both directions. For example, the charging terminals 910 and 920, and the sensing terminals 930 and 940 may be configured as pogo pins.

According to an embodiment of the disclosure, the logic circuit 905 may be electrically connected to the first and second sensing terminals 930 and 940 of the charger 900. The logic circuit 905 may control at least one switch based on a signal received through one of the first and second sensing terminals 930 and 940.

For example, when the first sensing terminal 930 contacts a part of the housing of the electronic device 101, the logic circuit 905 may receive at least one signal from the first sensing terminal 930. The second sensing terminal 940 may be accommodated in the groove of the electronic device 101, without contacting a part of the housing of the electronic device 101. The logic circuit 905 may control the switches 952 and 953 based on a signal received from the first sensing terminal 930. For example, the logic circuit 905 may apply a rated voltage (e.g., 5V) to the first charging terminal 910 and ground the second charging terminal 920 by controlling the switches 952 and 953.

When the second sensing terminal 940 contacts a part of the housing of the electronic device 101, the logic circuit 905 may receive at least one signal from the second sensing terminal 940. The first sensing terminal 930 may be accommodated in the groove of the electronic device 101, without contacting a part of the housing of the electronic device 101. The logic circuit 905 may control the switches 952 and 953 based on a signal received from the second sensing terminal 940. For example, the logic circuit 905 may apply a rated voltage (e.g., 5V) to the second charging terminal 920 and ground the first charging terminal 910 by controlling the switches 952 and 953.

With continued reference to FIGS. 10A, 10B and 10C, an embodiment of coupling the charger 900 to the electronic device 101 will be described in greater detail.

Figure 10A:
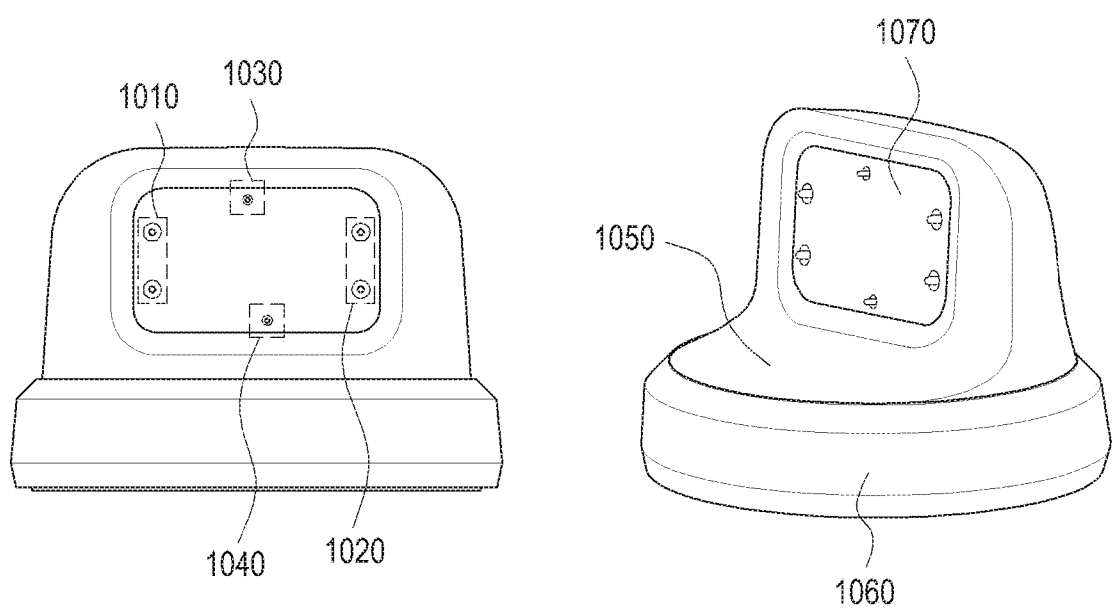
FIGS. 10A, 10B and 10C are views illustrating a structure of a charger and a layout of electrodes according to various embodiments of the disclosure.
Figure 10B:
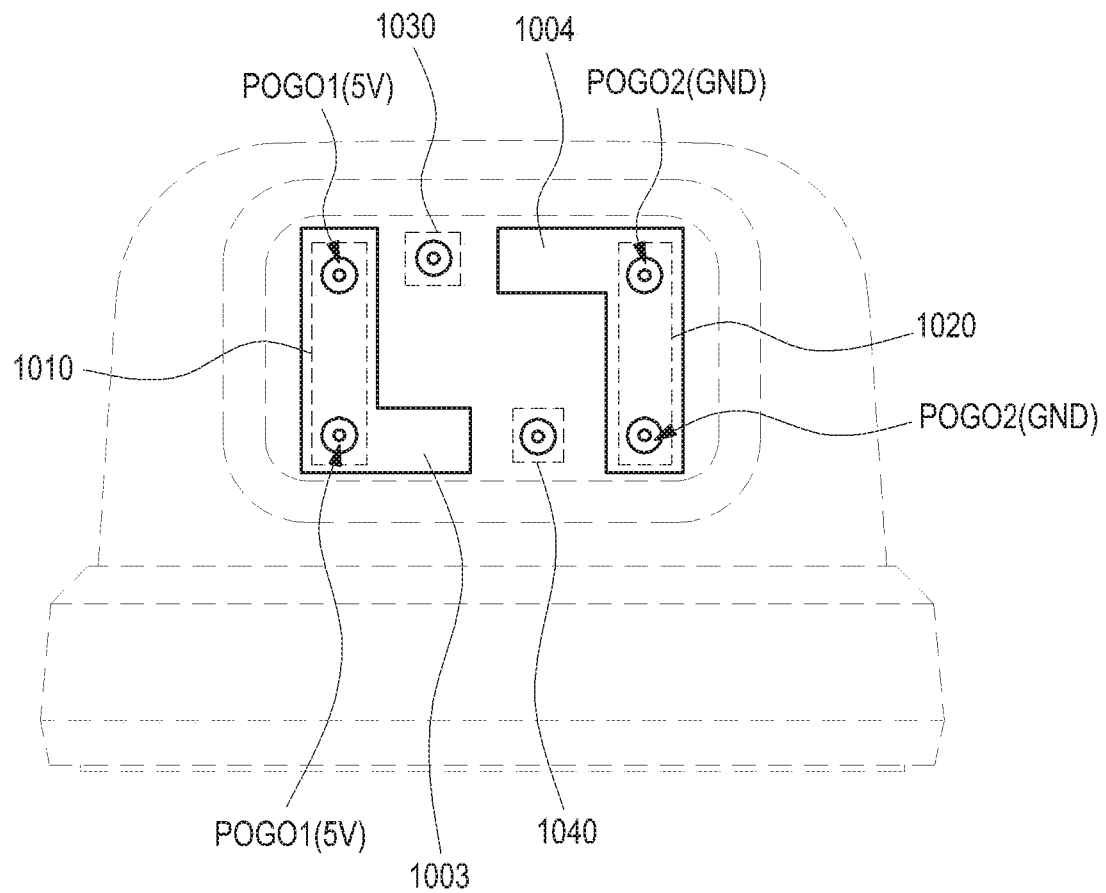
Figure 10C:
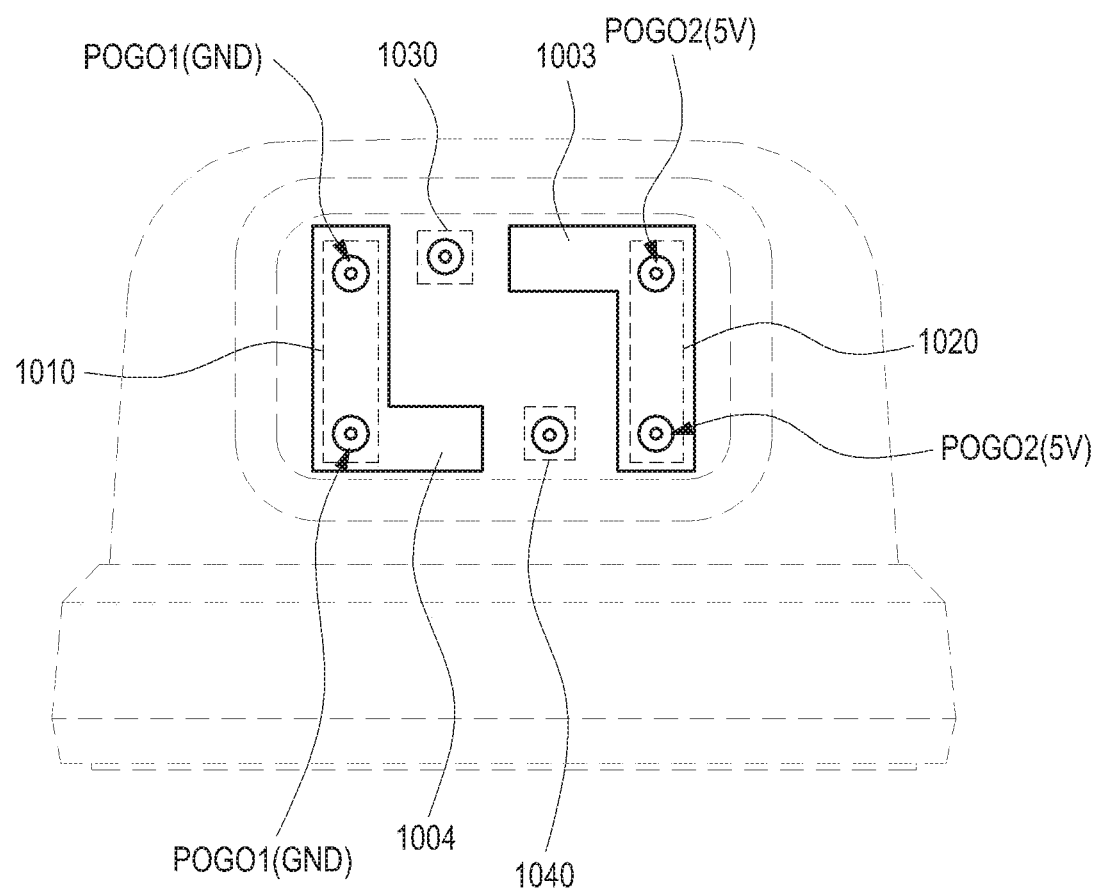

FIGS. 10A, 10B and 10C are views illustrating the structure of the charger 900, and an electrode layout according to various embodiments of the disclosure.

Referring to FIG. 10A, the charger 900 may include a first charging terminal 1010 (e.g., the first charging terminal 910 illustrated in FIG. 9), a second charging terminal 1020 (e.g., the second charging terminal 920 illustrated in FIG. 9), a first sensing terminal 1030 (e.g., the first sensing terminal 930 illustrated in FIG. 9), and a second sensing terminal 1040 (e.g., the second sensing terminal 940 illustrated in FIG. 9). The charger 900 may further include a cradle 1050 that supports an external device (e.g., the electronic device 101), a base 1060, and a coupling unit 1070.

According to an embodiment of the disclosure, an electronic device (e.g., the electronic device 101 illustrated in FIG. 1 or the electronic device 201 illustrated in FIG. 2) may be coupled to the charger 900, in order to charge a battery. The charging terminals 1010 and 1020 of the charger 900 may be brought into contact with electrodes (e.g., the electrodes 303 and 304 in FIG. 3) of the electronic device 101. For example, the first charging terminal 1010 of the charger 900 may contact a first electrode of the electronic device 101, and the second charging terminal 1020 of the charger 900 may contact a second electrode of the electronic device 101.

According to another embodiment of the disclosure, when the electronic device 101 and the charger 900 are coupled to each other, the sensing terminals 1030 and 1040 of the charger 900 may be accommodated in a groove (e.g., the groove 310 in FIG. 3) of the electronic device 101 or contact a part of the housing of the electronic device 101. For example, when the electronic device 101 and the charger 900 are coupled to each other in the first direction, the first sensing terminal 1030 may contact a part of the housing of the electronic device 101, whereas the second sensing terminal 1040 may be accommodated in the groove of the electronic device 101 without contacting a part of the housing. Further, when the electronic device 101 and the charger 900 are coupled to each other in the second direction opposite to the first direction, the first sensing terminal 1030 may be accommodated in the groove of the electronic device 101 without contacting a part of the housing, whereas the second sensing terminal 1040 may contact a part of the housing of the electronic device 101. If one of the first and second sensing terminals 1030 and 1040 of the charger 900 contacts the housing of the electronic device 101, a logic circuit (e.g., the logic circuit 905 illustrated in FIG. 9) of the charger 900 may acquire at least one signal through the contacting sensing terminal. The logic circuit of the charger 900 may control a switch of the charger 900 based on at least one signal generated from one of the first and second sensing terminals 1030 and 1040.

According to an embodiment of the disclosure, the charging terminals 1010 and 1020, and the sensing terminals 1030 and 1040 of the charger 900 may be configured as pogo pins. Therefore, when the charger 900 and the electronic device 101 are coupled to each other, at least a part of the charging terminal 1010, the charging terminal 1020, the sensing terminal 1030, or the sensing terminal 1040 of the charger 900 may contact the housing or an electrode of the electronic device 101.

FIG. 10B illustrates a case in which the charger 900 and the electronic device 101 are coupled to each other in the first direction.

Referring to FIG. 10B, the electronic device (e.g., the electronic device 101 illustrated in FIG. 1 or the electronic device 201 illustrated in FIG. 2) may include electrodes 1003 and 1004 exposed through at least a part of the housing of the electronic device 101. The electrodes 1003 and 1004 of the electronic device 101 may be used in charging the battery of the electronic device 101 by contacting the charging terminals 1010 and 1020 of the charger 900. For example, the first electrode 1003 of the electronic device 101 may contact the first charging terminal 1010 of the charger 900. Further, the second electrode 1004 of the electronic device 101 may contact the second charging terminal 1020 of the charger 900. In FIG. 10B, the electrodes 1003 and 1004 of the electronic device 101 coupled to the charger 900 are shown.

According to another embodiment of the disclosure, the electronic device 101 may include a groove (e.g., the groove 310 illustrated in FIG. 3) in at least a part of the housing of the electronic device 101. The groove of the electronic device 101 may accommodate the sensing terminal 1030 or 1040 of the charger 900, thereby preventing the sensing terminal 1030 or 1040 from being pressed by the housing of the electronic device 101.

For example, if the charger 900 and the electronic device 101 are coupled to each other in the first direction, the first sensing terminal 1030 may contact the housing of the electronic device 101, whereas the second sensing terminal 1040 may be accommodated in the groove of the electronic device 101. In this case, the first sensing terminal 1030 may be pressed by the housing of the electronic device 101, whereas the second sensing terminal 1040 may be accommodated in the groove of the electronic device 101 without being pressed.

If the logic circuit of the charger 900 determines that only the first sensing terminal 1030 is pressed, the logic circuit may apply a rated voltage (e.g., 5V) to the first charging terminal 1010 and connect the second charging terminal 1020 to a grounding terminal by controlling a switch in the charger 900.

FIG. 10C illustrates a case in which the charger 900 and the electronic device 101 are coupled to each other in the second direction.

Referring to FIG. 10C, the second electrode 1004 of the electronic device 101 may contact the first charging terminal 1010 of the charger 900. Further, the first electrode 1003 of the electronic device 101 may contact the second charging terminal 1020 of the charger 900. In FIG. 10C, the electrodes 1003 and 1004 of the electronic device 101 coupled to the charger 900 are shown.

According to another embodiment of the disclosure, if the charger 900 and the electronic device 101 are coupled to each other in the second direction, the first sensing terminal 1030 may be accommodated in the groove of the electronic device 101, whereas the second sensing terminal 1040 may contact the housing of the electronic device 101. In this case, the first sensing terminal 1030 may be accommodated in the groove of the electronic device 101 without being pressed, whereas the second sensing terminal 1040 may be pressed by the housing of the electronic device 101.

If the logic circuit of the charger 900 determines that only the second sensing terminal 1040 is pressed, the logic circuit may apply a rated voltage (e.g., 5V) to the second charging terminal 1020 and connect the first charging terminal 1010 to the grounding terminal by controlling the switch in the charger 900.

Figure 11:
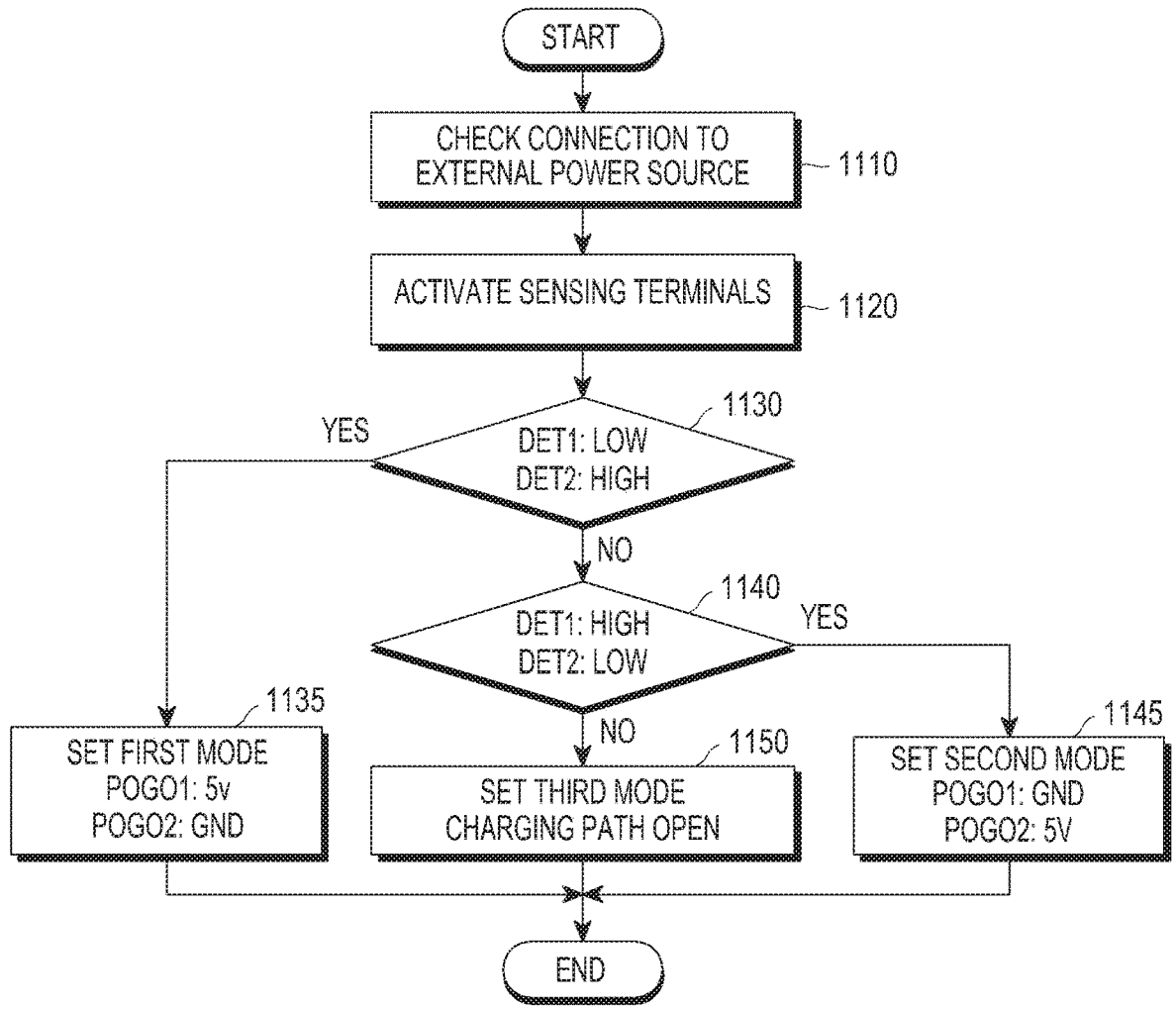
FIG. 11 is a flowchart illustrating a process of charging a battery of an electronic device in consideration of the direction of coupling between the electronic device and a charger according to an embodiment of the disclosure.

FIG. 11 is a flowchart illustrating a method for charging the battery of the electronic device 101 in consideration of the direction of coupling between the electronic device 101 and the charger 900 according to an embodiment of the disclosure.

An entity that performs the method may be a processor (e.g., the logic circuit 905 illustrated in FIG. 9) in the charger 900 including a charging terminal (e.g., the first charging terminal 910 and the second charging terminal 920 illustrated in FIG. 9), a sensing terminal (e.g., the first sensing terminal 930 and the second sensing terminal 940 illustrated in FIG. 9), at least one switch, and the processor (e.g., the logic circuit 905 illustrated in FIG. 9).

Referring to FIG. 11, the processor 905 may determine whether the charger 900 is coupled to an external power source that supplies power in operation 1110.

In operation 1120, the processor 905 may activate a first sensing terminal (e.g., the first sensing terminal 930 illustrated in FIG. 9) and a second sensing terminal (e.g., the second sensing terminal 940 illustrated in FIG. 9) which are used to sense the direction of coupling between the charger 900 and the electronic device (e.g., the electronic device 101 illustrated in FIG. 1 or the electronic device 201 illustrated in FIG. 2).

In operation 1130, the processor 905 may sense at least one signal received from the first and second sensing terminals. For example, the processor 905 may include an interface DET1 electrically connectable to the first sensing terminal, and an interface DET2 electrically connectable to the second sensing terminal. If a low signal is sensed at the interface DET1 corresponding to the first sensing terminal, and a high signal is sensed at the interface DET2 corresponding to the second sensing terminal, the processor 905 may determine that the first sensing terminal is pressed, and the second sensing terminal is not pressed.

Referring to the embodiment of FIG. 9, if either of the first sensing terminal 930 and the second sensing terminal 940 is not pressed, a switch provided at each of the first and second sensing terminals may be maintained in an open state. In this case, a rated voltage (e.g., 5V) output from a power source may be applied to the interface DET1 corresponding to the first sensing terminal and the interface DET2 corresponding to the second sensing terminal. When the rated voltage output from the power source is applied to the interface DET1 and the interface DET2 in this manner, the processor 905 may sense a high signal at each of the interfaces.

If the first sensing terminal 930 or the second sensing terminal 940 is pressed, one of the switch provided at the first sensing terminal and the switch provided at the second sensing terminal may be closed. For example, if the first sensing terminal contacts the housing of the electronic device, the switch provided at the first sensing terminal may be closed, and thus the interface DET1 corresponding to the first sensing terminal may be grounded. In this manner, the processor 905 may sense a low signal through the grounded interface DET1.

If a low signal is sensed at the interface DET1 and a high signal is sensed at the interface DET2, the processor 905 may perform operation 1135.

In operation 1135, the processor 905 may set the charger 900 to a first mode. In the first mode, a switch in the charger 900 may be controlled so that a rated voltage may be applied to the first charging terminal (e.g., the first charging terminal 910 illustrated in FIG. 9), and the second charging terminal (e.g., the second charging terminal 210 illustrated in FIG. 9) may be grounded.

If the condition of operation 1130 is not satisfied, the processor 905 may perform operation 1140.

In operation 1140, the processor 905 may sense at least one signal received from the first and second sensing terminals. For example, the processor 905 may include the interface DET1 electrically connectable to the first sensing terminal and the interface DET2 electrically connectable to the second sensing terminal. If a high signal is sensed at the interface DET1 corresponding to the first sensing terminal, and a low signal is sensed at the interface DET2 corresponding to the second sensing terminal, the processor 905 may determine that the first sensing terminal is not pressed, and the second sensing terminal is pressed, and perform operation 1145.

In operation 1145, the processor 905 may set the charger 900 to a second mode. In the second mode, the switch in the charger 900 may be controlled so that the first charging terminal may be grounded, and a rated voltage may be applied to the second charging terminal (e.g., the second charging terminal 210 illustrated in FIG. 9).

If the condition of operation 1140 is not satisfied, the processor 905 may perform operation 1150.

In operation 1150, the processor 905 may set the charger 900 to a third mode. For example, if either of the condition of operation 1130 and the condition of operation 1140 is not satisfied, the processor 905 may determine that the charger 900 and the electronic device 101 have not been coupled to each other normally. Thus, to prevent short circuit which may occur to a circuit in the charger 900, all circuits used for charging may be opened by controlling the switch in the charger 900.

Figure 12:
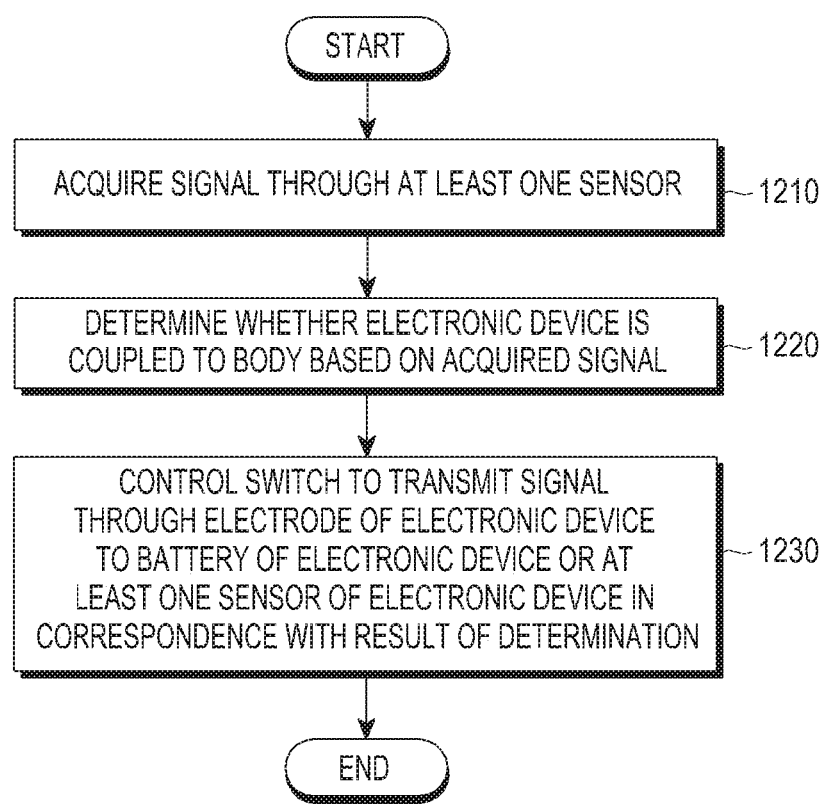
FIG. 12 is a flowchart illustrating a process of controlling an electronic device according to an embodiment of the disclosure.

FIG. 12 is a flowchart illustrating a method for controlling an electronic device according to an embodiment of the disclosure.

Referring to FIG. 12, an entity that performs the method may be a processor (e.g., the processor 120 illustrated in FIG. 1 or the processor 210 illustrated in FIG. 2) in an electronic device (e.g., the electronic device 101 illustrated in FIG. 1 or the electronic device 201 illustrated in FIG. 2) including at least one electrode (e.g., the electrodes 301, 302, 303, and 304 illustrated in FIG. 3), at least one sensor (e.g., the sensors 340 and 342 illustrated in FIG. 3), and the processor (e.g., the processor 120 illustrated in FIG. 1 or the processor 210 illustrated in FIG. 2).

Referring to FIG. 12, in operation 1210, the processor 120 may acquire a signal through the at least one sensor. For example, the processor 120 may acquire at least one signal through the grip sensor of the electronic device 101.

In operation 1220, the processor 120 may determine whether the electronic device 101 is coupled to a body, based on the acquired at least one signal. For example, the grip sensor may sense a capacitance variation caused by an object located within a predetermined distance from the electronic device 101. The processor 120 may measure the dielectric constant of the object around the electronic device 101 based on the capacitance variation sensed by the grip sensor. The processor 120 may determine whether the electronic device 101 is coupled to the body based on the measured dielectric constant.

In operation 1230, the processor 120 may control at least one switch of the electronic device 101 in correspondence with the result of the determination in operation 1120 in order to transmit a signal received through an electrode of the electronic device 101 to the battery of the electronic device 101 or the at least one sensor of the electronic device 101. For example, if determining that the electronic device 101 is coupled to the body, the processor 120 may electrically connect the electrode of the electronic device 101 to the at least one sensor of the electronic device 101 by controlling at least one switch. If determining that the electronic device 101 is not coupled to the body, the processor 120 may electrically connect the electrode of the electronic device 101 to a charger IC (e.g., the charger IC

495 illustrated in FIG. 4) by controlling the at least one switch, so that the battery of the electronic device 101 may be charged.

Figure 13:
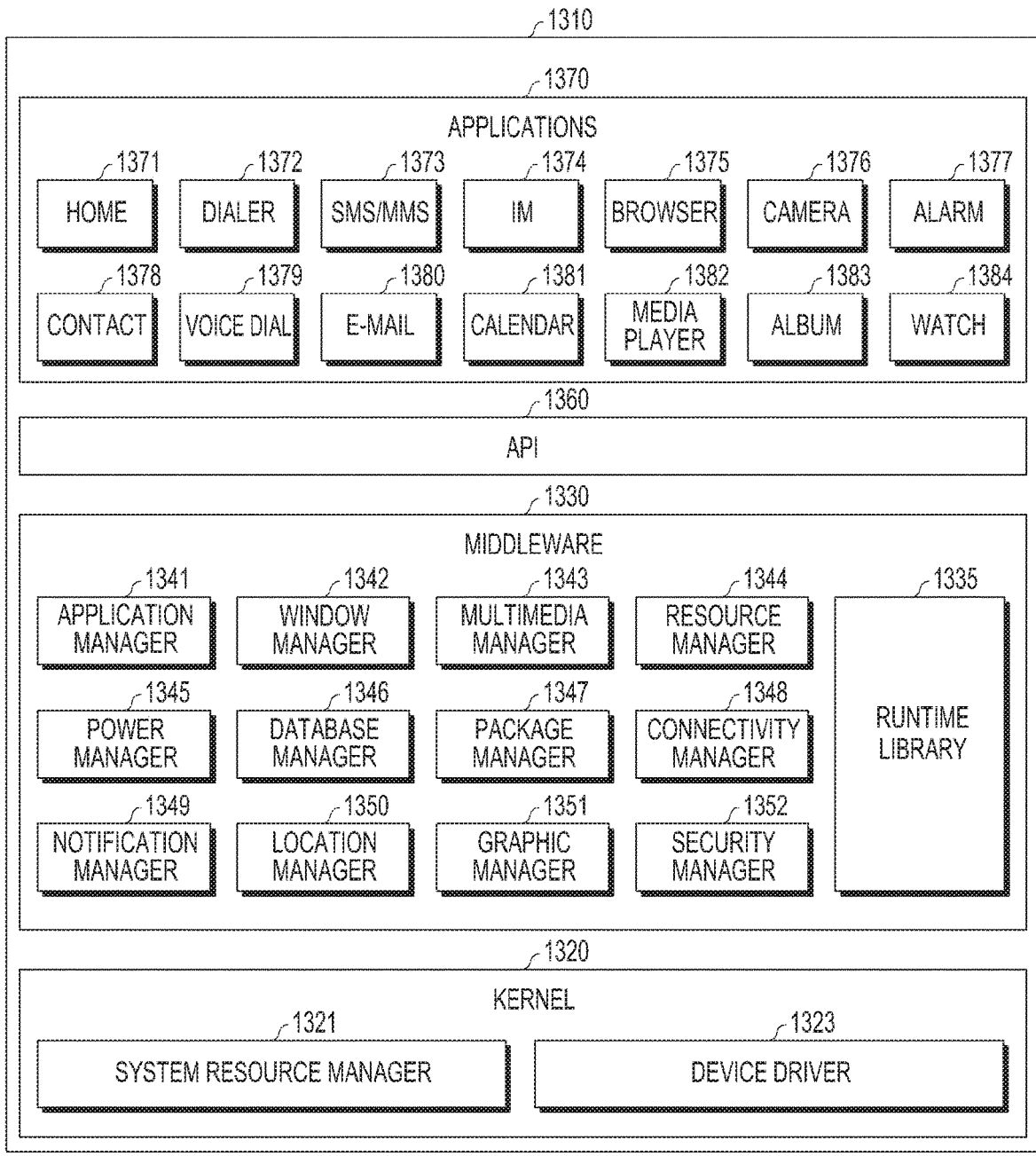
FIG. 13 is a block diagram illustrating a programming module according to an embodiment of the disclosure.

FIG. 13 is a block diagram of a programming module according to an embodiment of the disclosure.

Referring to FIG. 13, a programming module 1310 (e.g., a program 140) may include an OS that controls resources related to an electronic device (e.g., the electronic device 101) and/or various applications executed on the OS (e.g., the application programs 147). The OS may be Android™, iOS™, Windows™, Symbian™, Tizen™, or Bada™.

Referring to FIG. 13, the programming module 1310 may include a kernel 1320 (e.g., the kernel 141), middleware 1330 (e.g., the middleware 143), an API 1360 (e.g., the API 145), and/or applications 1370 (e.g., the application programs 147). At least a part of the programming module 1310 may be preloaded on the electronic device or downloaded from an external electronic device (e.g., the electronic device 102 or 104, or the server 106).

The kernel 1320 may include, for example, a system resource manager 1321 and/or a device driver 1323. The system resource manager 1321 may control, allocate, or deallocate system resources. The system resource manager 1321 may include a process manager, a memory manager, or a file system manager. The device driver 1323 may include a display driver, a camera driver, a Bluetooth driver, a shared memory driver, a USB driver, a keypad driver, a WiFi driver, an audio driver, or an inter-process communication (IPC) driver.

The middleware 1330 may provide a function required commonly for the applications 1370 or provide various functionalities to the applications 1370 through the API 1360 so that the applications 1370 may use limited system resources available within the electronic device. The middleware 1330 may include at least one of a runtime library 1335, an application manager 1341, a window manager 1342, a multimedia manager 1343, a resource manager 1344, a power manager 1345, a database manager 1346, a package manager 1347, a connectivity manager 1348, a notification manager 1349, a location manager 1350, a graphic manager 1351, or a security manager 1352.

The runtime library 1335 may include a library module that a compiler uses to add a new function in a programming language during execution of an application 1370. The runtime library 1335 may perform input/output management, memory management, or arithmetic function processing.

The application manager 1341 may manage the life cycle of the applications 1370. The window manager 1342 may manage GUI resources used for a screen. The multimedia manager 1343 may determine formats required to play back media files and may encode or decode a media file using a codec suitable for the format of the media file. The resource manager 1344 may manage a source code or a memory space. The power manager 1345 may manage a battery capacity, temperature, or a power source and provide power information required for an operation of the electronic device, using corresponding information. The power manager 1345 may interact with a basic input/output system (BIOS). The database manager 1346 may generate, search, or modify a database to be used for the applications 1370. The package manager 1347 may manage installation or update of an application distributed as a package file. The connectivity manager 1348 may manage wireless connectivity. The notification manager 1349 may provide a user with an event such as message arrival, a schedule, a proximity notification, or the like. The location manager 1350 may mange position information about the electronic device. The graphic manager 1351 may manage graphical effects to be provided to the user or related user interfaces. The security manager 1352 may provide system security or user authentication. In an embodiment, the middleware 1330 may include a telephony manager to manage a voice or video call function of the electronic device, or a middleware module for combining functions of the above-described components. The middleware 1330 may provide a customized module for each OS type. The middleware 1330 may dynamically delete a part of the existing components or add a new component.

The API 1360 is a set of API programming functions, which may be configured differently according to an OS. For example, in the case of Android or iOS, one API set may be provided per platform, whereas in the case of Tizen, two or more API sets may be provided per platform.

The applications 1370 may include home 1371, dialer 1372, short message service/multimedia messaging service (SMS/MMS) 1373, instant message (IM) 1374, browser 1375, camera 1376, alarm 1377, contacts 1378, voice dial 1379, email 1380, calendar 1381, media player 1382, album 1383, watch 1384, health care (e.g., measurement of an exercise amount or a glucose level), or an application for providing environment information (e.g., information about atmospheric pressure, humidity, or temperature). The applications 1370 may include an information exchange application capable of supporting information exchange between the electronic device and an external electronic device. The information exchange application may include, for example, a notification relay application for transmitting specific information to the external electronic device or a device management application for managing the external electronic device. For example, the notification relay application may transmit notification information generated from another application to the external electronic device, or receive notification information from the external electronic device and transmit the received notification information to a user. The device management application may install, delete, or update functions of the external electronic device communicating with the electronic device (e.g., turn-on/turn-off of the external electronic device (or a part of its components) or control of the brightness or resolution of the display), or an application executed in the external electronic device. The applications 1370 may include an application (e.g., a health care application of a mobile medical equipment) designated according to a property of the external electronic device. The applications 1370 may include an application received from an external electronic device. At least a part of the programming module 1310 may be realized (implemented) in software, firmware, hardware (e.g., the processor 210), or a combination of at least two of them, and may include a module, a program, a routine, a set of instructions, or a process to execute one or more functions.

According to various embodiments of the disclosure, a method for controlling a wearable electronic device including at least one electrode may include determining whether the wearable electronic device is coupled to a body, based on a signal acquired through at least one sensor of the wearable electronic device, and controlling a switch of the wearable electronic device to connect a charger circuit of the wearable electronic device or the at least one sensor to the at least one electrode in correspondence with a result of the determination.

According to various embodiments of the disclosure, the method for controlling a wearable electronic device including at least one electrode may include, if it is determined that the wearable electronic device is coupled to the body, controlling the switch to connect the at least one sensor to the at least one electrode, and generating biometric information related to the body based on a signal acquired through the at least one electrode.

According to various embodiments of the disclosure, the method for controlling a wearable electronic device including at least one electrode may include, if it is determined that the wearable electronic device is not coupled to the body, controlling the switch to connect the charger circuit to the at least one electrode.

According to various embodiments of the disclosure, the method for controlling a wearable electronic device including at least one electrode may include controlling the switch to connect the charger circuit to the at least one electrode, based on at least one signal received from an external device through a terminal disposed inside a groove formed towards the inside of the wearable electronic device on at least a part of a housing of the wearable electronic device.

According to various embodiments of the disclosure, the method for controlling a wearable electronic device including at least one electrode may include controlling the switch to connect the charger circuit to the at least one electrode in a first mode, if a first signal is received from the external device through the terminal, and controlling the switch to connect the charger circuit to the at least one electrode in a second mode, if a second signal is received from the external device through the terminal.

According to various embodiments of the disclosure, an electronic device (e.g., the charger 900 illustrated in FIG. 9) configured to allow an external device (e.g., the electronic device 101 illustrated in FIG. 1 or the electronic device 201 illustrated in FIG. 2) to be detachably cradled thereon, may include a housing, a power interface (the OVP 960 illustrated in FIG. 9) provided inside the housing, and configured to change power received from an external power source to power of a predetermined level and output the power of the predetermined level, a plurality of first conductive members (e.g., the charging terminal 910 or 920 illustrated in FIG. 9) connected electrically to the power interface, and configured to transfer power externally, a plurality of second conductive members (e.g., the sensing terminal 930 or 940 illustrated in FIG. 9) configured to determine whether the electronic device and the external device have been coupled to each other, and a control circuit (e.g., the logic circuit 905 illustrated in FIG. 9) connected electrically to the power interface, the plurality of first conductive members, and the plurality of second conductive members.

According to various embodiments of the disclosure, in the electronic device 900 configured to allow an external device to be detachably cradled thereon, the control circuit 905 may be configured to identify at least one of the plurality of second conductive members, contacting at least a part of the electronic device, and to control a switch corresponding to the identified at least one second conductive member to connect at least a part of the plurality of first conductive members to the power interface.

According to various embodiments of the disclosure, in the electronic device 900 configured to allow an external device to be detachably cradled thereon, if a first member (e.g., the first sensing terminal 930 illustrated in FIG. 9) among the plurality of second conductive members is identified as contacting the at least part of the external device, the control circuit 905 may be configured to control the switch to connect the plurality of first conductive members to the power interface in a first mode, and if a second member (e.g., the second sensing terminal 940 illustrated in FIG. 9) among the plurality of second conductive members is identified as contacting the at least part of the external device, the control circuit 905 may be configured to control the switch to connect the plurality of first conductive members to the power interface in a second mode.

According to various embodiments of the disclosure, in the electronic device 900 configured to allow an external device to be detachably cradled thereon, if both of the first member (e.g., the first sensing terminal 930 illustrated in FIG. 9) and the second member (e.g., the second sensing terminal 940 illustrated in FIG. 9) are identified as contacting the at least part of the external device, the control circuit 905 may be configured to control the switch not to connect the plurality of first conductive members to the power interface.

According to various embodiments of the disclosure, in the electronic device 900 configured to allow an external device to be detachably cradled thereon, at least one of the plurality of first conductive members and the plurality of second conductive members may be configured as a pogo connector including a pogo pin.

According to various embodiments of the disclosure, a wearable electronic device (e.g., the electronic device 101 illustrated in FIG. 1 or the electronic device 201 illustrated in FIG. 2) may include a housing including a first surface facing in a first direction, a second surface facing in a second direction, and a side surface surrounding at least a part of a space between the first surface and the second surface, a first conductive member (e.g., the electrode 301 or 302 illustrated in FIG. 3) exposed outwards from the first surface of the housing, a second conductive member (e.g., the electrode 303 or 304 illustrated in FIG. 3) exposed outwards from the second surface of the housing, a charger circuit (e.g., the power management module 295 illustrated in FIG. 2) provided inside the housing, and connected electrically to at least one of the first conductive member or the second conductive member, a first sensor (e.g., the sensor module 240 illustrated in FIG. 2) provided inside the housing, and connected electrically to at least one of the first conductive member or the second conductive member, a control circuit (e.g., the processor 120 illustrated in FIG. 1 or the processor 210 illustrated in FIG. 2) connected electrically to the first conductive member, the second conductive member, and the charger circuit, and a coupling member (e.g., the coupling member 350 illustrated in FIG. 3) connected to a part of the housing, and configured to detachably couple the wearable electronic device to a part of a user's body.

According to various embodiments of the disclosure, in the wearable electronic device 101, the first conductive member may include a first electrode and a second electrode, and the second conductive member may include a third electrode and a fourth electrode. The first sensor may be configured to acquire physical information about the user, based on an external signal (e.g., at least one of current, voltage, resistance, or capacitance) acquired through at least a part of the first electrode, the second electrode, the third electrode, or the fourth electrode.

According to various embodiments of the disclosure, in the wearable electronic device 101, the first conductive member may include a first electrode and a second electrode, and the second conductive member may include a third electrode and a fourth electrode. The charger circuit may be configured to charge a battery of the wearable electronic device, based on an external signal (e.g., at least one of current, voltage, resistance, or capacitance) acquired through at least a part of the first electrode, the second electrode, the third electrode, or the fourth electrode.

According to various embodiments of the disclosure, the wearable electronic device 101 may further include a first groove formed in the second direction on a part of the first surface of the housing, and a first terminal disposed inside the first groove, or a second groove formed in the first direction on a part of the second surface of the housing, and a second terminal disposed inside the second groove. The control circuit 120 may be configured to control at least one switch provided inside the wearable electronic device, based on at least one signal received from an external device through the first terminal or the second terminal.

According to various embodiments of the disclosure, in the wearable electronic device 101, the control circuit 102 may be configured to determine whether the wearable electronic device is coupled to a body, based on a signal acquired through the first sensor (e.g., the biometric sensor 240I illustrated in FIG. 2) or a second sensor (e.g., the grip sensor 240F illustrated in FIG. 2 or the proximity sensor 240G illustrated in FIG. 2), and to control at least one switch provided inside the wearable electronic device to connect the charger circuit or the first sensor to at least one of the first conductive member or the second conductive member based on a result of the determination.

According to various embodiments of the disclosure, in the wearable electronic device 101, if the control circuit 120 determines that the wearable electronic device is coupled to the body, the control circuit may be configured to control the at least one switch to connect the first sensor to at least one of the first conductive member or the second conductive member, and if the control circuit determines that the wearable electronic device is not coupled to the body, the control circuit may be configured to control the at least one switch to connect the charger circuit to at least one of the first conductive member or the second conductive member.

As is apparent from the foregoing description, an electronic device according to an embodiment of the disclosure may acquire physical information or health information about a user, and charge a battery, through at least one electrode provided in the electronic device. Since the electronic device according to the embodiment of the electronic device may charge the battery through the electrode configured to acquire physical information or health information about a user, there is no need for an additional contact terminal for charging the battery. Accordingly, limitations imposed on a design process for the electronic device may be reduced.

A charger according to an embodiment of the disclosure may supply power to an electronic device irrespective of a direction in which the charger and the electronic device are electrically coupled to each other. If the charger supporting charging irrespective of a coupling direction is provided in this manner, the electronic device does not need for an additional component for preventing reverse insertion. Accordingly, miniaturization of the electronic device may be facilitated.

The term "module" as used herein may include its ordinary meaning including, for example, a unit of one, or a combination of two or more of hardware, software, and firmware. The term "module" may be used interchangeably with terms such as, for example, unit, logic, logical block, component or circuit. A "module" may be the smallest unit of an integrated part or a portion thereof. A 'module' may be the smallest unit for performing one or more functions, or a portion thereof. A "module" may be implemented mechanically, or electronically. For example, a "module" may include at least one of a known, or to-be-developed, application-specific integrated circuit (ASIC) chip, field-programmable gate arrays (FPGAs), or programmable logic devices that perform certain operations.

At least a part of apparatuses (e.g., modules or their functions) or methods (e.g., operations) according to various embodiments may be implemented as commands stored in a computer-readable storage medium (e.g., the memory 130), in the form of a programming module. When the commands are executed by a processor (e.g., the processor 120), one or more processors may execute functions corresponding to the commands. The computer-readable medium may include hard disk, floppy disk, magnetic media (e.g., magnetic tape), optical media (e.g., compact disc read-only memory (CD-ROM)), DVD, magneto-optical media (e.g., floptical disk), and the like. Instructions may include a code that may be produced by a compiler or a code that may be executed by an interpreter. A module or a programming module according to various embodiments may include one or more of the above-described components, may omit a portion thereof, or may include additional components. Operations that are performed by a module, a programming module or other components according to various embodiments may be processed in a serial, parallel, repetitive or heuristic manner. Also, some operations may be performed in a different order or omitted, or additional operations may be added.

Each of the above-described components may include one or more parts, and the name of the component may vary with the type of an electronic device. According to various embodiments, some component may be omitted from or added to the electronic device. Further, one entity may be configured by combining a part of the components of the electronic device, to thereby perform the same functions of the components prior to the combining.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A wearable electronic device comprising:
   a housing;
   a groove formed in at least a part of the housing, facing towards an inside of the wearable electronic device;
   a terminal disposed inside the groove;
   at least one electrode exposed outwards from one surface of the housing;
   a battery provided inside the housing;
   a charger circuit connected electrically to the battery;
   at least one sensor;
   a switch configured to connect the charger circuit or the at least one sensor to the at least one electrode; and
   at least one processor connected electrically to the charger circuit, the at least one sensor, and the switch,
   wherein the at least one processor is configured to:
      determine whether the wearable electronic device is coupled to a body, based on a signal acquired through the at least one sensor, and
      control the switch to connect the charger circuit or the at least one sensor to the at least one electrode based on the determination,
   wherein the at least one electrode comprises a first electrode and a second electrode,
   wherein when a first signal is received from an external device through the terminal based on a first direction in which the wearable electronic device is coupled to the external device, the at least one processor is further configured to control the switch to connect the charger circuit to the first electrode, and wherein, when a second signal is received from the external device through the terminal based on a second direction in which the wearable electronic device is coupled to the external device, the at least one processor is further configured to control the switch to connect the charger circuit to the second electrode.

2. The wearable electronic device of claim 1, wherein, when the at least one processor determines that the wearable electronic device is coupled to the body, the at least one processor is further configured to:

control the switch to connect the at least one sensor to the at least one electrode, and generate biometric information related to the body based on a signal acquired through the at least one electrode.

3. The wearable electronic device of claim 1, wherein the housing comprises:

a first surface facing in a first direction, a second surface facing in a second direction opposite to the first direction, and a side surface surrounding at least a part of a space between the first surface and the second surface, and wherein the at least one electrode comprises:

the first electrode and the second electrode exposed outwards from the first surface of the housing, and a third electrode and a fourth electrode exposed outwards from the second surface of the housing.

4. The wearable electronic device of claim 3, wherein the at least one sensor comprises:

a first sensor connected electrically to the at least one electrode, and configured to receive a signal through the at least one electrode, and a second sensor configured to receive an external signal through at least one of the first surface or the second surface of the housing.

5. The wearable electronic device of claim 4, wherein the first sensor comprises at least one of a bioelectrical impedance analysis (BIA) sensor, an electrocardiogram (ECG) sensor, or a galvanic skin response (GSR) sensor, and wherein the second sensor comprises at least one of an optical sensor or a grip sensor.

6. The wearable electronic device of claim 4, wherein the first electrode and second electrode exposed outwards from the first surface of the housing, or the third electrode and fourth electrode exposed outwards from the second surface of the housing are "L-shaped" or "U-shaped" electrodes symmetrical to each other, surrounding a periphery of the second sensor exposed outwards.

7. A wearable electronic device comprising:

a housing comprising:

a first surface facing in a first direction, a second surface facing in a second direction opposite to the first direction, at least one of a first groove formed in the second direction on a part of the first surface of the housing and a first terminal disposed inside the first groove, or a second groove formed in the first direction on a part of the second surface of the housing and a second terminal disposed inside the second groove, and a side surface surrounding at least a part of a space between the first surface and the second surface;

a first conductive member exposed outwards from the first surface of the housing;

a second conductive member exposed outwards from the second surface of the housing;

a charger circuit provided inside the housing, and connected electrically to at least one of the first conductive member or the second conductive member;

a first sensor provided inside the housing, and connected electrically to at least one of the first conductive member or the second conductive member;

a control circuit connected electrically to the first conductive member, the second conductive member, the charger circuit, and the first sensor; and a coupling member connected to a part of the housing, and configured to detachably couple the wearable electronic device to a part of a user's body, wherein the first conductive member comprises a first electrode and a second electrode, wherein the second conductive member comprises a third electrode and a fourth electrode, wherein, when a first signal is received from an external device through the first terminal or the second terminal based on a first direction in which the wearable electronic device is coupled to the external device, the control circuit is configured to control at least one switch provided inside the wearable electronic device, to connect the charger circuit to the first electrode or the third electrode, and wherein, when a second signal is received from the external device through the first terminal or the second terminal based on a second direction in which the wearable electronic device is coupled to the external device, the control circuit is further configured to control the at least one switch to connect the charger circuit to the second electrode or the fourth electrode.

8. The wearable electronic device of claim 7, wherein the first sensor is configured to acquire physical information about the user, based on an external signal acquired through at least a part of the first electrode, the second electrode, the third electrode, or the fourth electrode.

9. The wearable electronic device of claim 7, wherein the charger circuit is configured to charge a battery of the wearable electronic device, based on an external signal acquired through at least a part of the first electrode, the second electrode, the third electrode, or the fourth electrode.

10. The wearable electronic device of claim 7, wherein the control circuit is configured to:

determine whether the wearable electronic device is coupled to a body, based on a signal acquired through the first sensor or a second sensor, and control at least one switch provided inside the wearable electronic device to connect the charger circuit or the first sensor to at least one of the first conductive member or the second conductive member based on a result of the determination.

11. The wearable electronic device of claim 10, wherein, when the control circuit determines that the wearable electronic device is coupled to the body, the control circuit is further configured to control the at least one switch to connect the first sensor to at least one of the first conductive member or the second conductive member, and wherein, when the control circuit determines that the wearable electronic device is not coupled to the body, the control circuit is further configured to control the at least one switch to connect the charger circuit to at least one of the first conductive member or the second conductive member.

\* \* \* \* \*